United States Patent
Hoang et al.

(10) Patent No.: US 10,065,074 B1
(45) Date of Patent: Sep. 4, 2018

(54) TRAINING SYSTEMS WITH WEARABLE SENSORS FOR PROVIDING USERS WITH FEEDBACK

(71) Applicant: Enflux Inc., Cupertino, CA (US)

(72) Inventors: Doug Hoang, Cupertino, CA (US); Elijah J. Schuldt, Cupertino, CA (US)

(73) Assignee: Enflux, Inc.

( * ) Notice: Subject to any disclaimer, the term of this patent is extended or adjusted under 35 U.S.C. 154(b) by 0 days.

(21) Appl. No.: 14/968,411

(22) Filed: Dec. 14, 2015

Related U.S. Application Data

(60) Provisional application No. 62/091,136, filed on Dec. 12, 2014.

(51) Int. Cl.
| | |
|---|---|
| *A41D 13/01* | (2006.01) |
| *A63B 24/00* | (2006.01) |
| *A41B 1/08* | (2006.01) |
| *A41D 1/00* | (2018.01) |
| *A41D 1/04* | (2006.01) |
| *A41D 19/00* | (2006.01) |
| *G09B 19/00* | (2006.01) |

(Continued)

(52) U.S. Cl.
CPC ............ *A63B 24/0003* (2013.01); *A41B 1/08* (2013.01); *A41D 1/005* (2013.01); *A41D 1/04* (2013.01); *A41D 19/0027* (2013.01); *A63B 24/0062* (2013.01); *G01P 1/02* (2013.01); *G08B 5/36* (2013.01); *G09B 19/003* (2013.01); *G09B 19/0038* (2013.01); *A63B 2220/40* (2013.01); *A63B 2220/803* (2013.01); *A63B 2220/83* (2013.01); *A63B 2220/89* (2013.01)

(58) Field of Classification Search
CPC ... A63B 24/0003; A63B 24/0062; A41B 1/08; A41D 1/005; A41D 1/04; A41D 19/0027; G01P 1/02; G08B 5/36; G09B 19/003; G09B 19/0038
USPC ........... 340/573.1, 572.1; 361/679.03, 679.3; 600/301, 546, 595; 73/865.4; 702/150
See application file for complete search history.

(56) References Cited

U.S. PATENT DOCUMENTS

| | | | | |
|---|---|---|---|---|
| 5,567,040 | A | * | 10/1996 | Tabanera ............... A41D 13/01 362/103 |
| 6,563,424 | B1 | * | 5/2003 | Kaario .................... G06F 1/163 340/572.1 |

(Continued)

*Primary Examiner* — Firmin Backer
*Assistant Examiner* — Munear Akki
(74) *Attorney, Agent, or Firm* — Nigamnarayan Acharya; Lewis Brisbois Bisgaard & Smith LLP

(57) ABSTRACT

A training system based on mobile technology and kinematics of human motion characterizes, analyzes, and supplies feedback to a user based on the user's movements. The training system includes a garment having a sensor control module connected to multiple sensor nodes via electrically-conductive fabric running along parts portions of the garment. The sensor module/nodes can communicate through the conductive fabric. The sensor nodes acquire motion and/or physiologic readings that are wirelessly transmitted to a mobile computing device that runs an application that analyzes the data and provides visual (e.g., graphs, 3D avatar) and audio feedback (e.g., voice prompts). Vibration motors and LEDs/electroluminescent fabric in the garment also provide notifications and alerts. The triple layer of garment, conductive fabric, and sensor module/sensor node are sealed against contaminants, allowing the garment to be washable.

29 Claims, 24 Drawing Sheets

(51) Int. Cl.
*G08B 5/36* (2006.01)
*G01P 1/02* (2006.01)

(56) References Cited

U.S. PATENT DOCUMENTS

| | | | | |
|---|---|---|---|---|
| 8,313,378 | B1* | 11/2012 | Snyder | A63B 22/18 |
| | | | | 463/36 |
| 9,075,435 | B1* | 7/2015 | Noble | G06F 3/013 |
| 2004/0145493 | A1* | 7/2004 | O'Connor | A61B 5/1118 |
| | | | | 340/870.09 |
| 2007/0038057 | A1* | 2/2007 | Nam | A61B 5/04085 |
| | | | | 600/388 |
| 2009/0062092 | A1* | 3/2009 | Mortimer | A63B 24/00 |
| | | | | 482/142 |
| 2011/0257928 | A1* | 10/2011 | Cunningham | A61B 5/1116 |
| | | | | 702/150 |
| 2012/0271143 | A1* | 10/2012 | Aragones | G06F 19/3481 |
| | | | | 600/407 |
| 2015/0045699 | A1* | 2/2015 | Mokaya | A61B 5/0024 |
| | | | | 600/595 |
| 2015/0075303 | A1* | 3/2015 | Connor | A61B 5/1126 |
| | | | | 73/865.4 |
| 2015/0305674 | A1* | 10/2015 | McPherson | A61B 5/1455 |
| | | | | 600/301 |
| 2015/0309563 | A1* | 10/2015 | Connor | G06F 3/011 |
| | | | | 73/865.4 |
| 2016/0058376 | A1* | 3/2016 | Baek | A61B 5/721 |
| | | | | 340/870.07 |

* cited by examiner

TRAINING SYSTEMS WITH WEARABLE SENSORS FOR PROVIDING USERS WITH FEEDBACK

CROSS-REFERENCE TO RELATED APPLICATIONS

This application claims priority under 35 USC § 119(e) to U.S. Provisional Patent Application 62/091,136 filed Dec. 12, 2014, the entirety of which is incorporated by reference herein.

FIELD OF THE INVENTION

This document concerns an invention relating generally to systems and methods of measuring, reporting, and guiding performance related to motion, posture, and form during athletic or medical-related movements and activities using wearable personal sensors that wirelessly communicate with computing devices and provide feedback.

BACKGROUND OF THE INVENTION

Traditionally, a user seeking feedback on his or her posture, movement, and technique during exercise, or while playing sports, would employ a trainer or coach to observe the user and provide feedback on his or her movements. The coach or trainer would often set up a camera to video record the user's movements in a specific environment for subsequent review. But this setup process can be tedious and the camera equipment can be very expensive, and hiring a trainer or coach can be very costly. Also, analysis of a video replay of a movement does not allow for real-time feedback. Moreover, even experienced trainers and coaches can miss day-to-day differences, incremental changes, and small errors that, at least over time, can lead to errors, inefficiencies, and/or injuries. What is needed is a system that can be used in a variety of places without time consuming or expensive setup processes, and that can provide precise real-time feedback.

SUMMARY OF THE INVENTION

The invention, which is defined by the claims set forth at the end of this document, is directed to training systems which at least partially alleviate the aforementioned problems. A basic understanding of some of the features of preferred versions of the invention can be attained from a review of the following brief summary of the invention, with more details being provided elsewhere in this document. To assist in the reader's understanding, the following review makes reference to the accompanying drawings (which are briefly reviewed in the "Brief Description of the Drawings" section following this Summary section of this document).

Exemplary versions of the invention enable people to enhance or maximize the benefits of time spent exercising at a gymnasium or elsewhere, reduce injuries, train more optimally for sports and other athletic movements, and evaluate and guide movements for rehabilitation or other medical reasons. One or more garments (such as gym shirts and pants) with sensors woven into the fabric thereof acquire data on motion to analyze full body form during athletic and other movements. The garments with sensors can connect and transmit movement data to a wireless-enabled computing device having a software application that can provide real-time visual and audio feedback during and after exercise routines. The feedback allows the user to better understand inefficiencies, and improve their technique in order to reduce or avoid injuries and achieve performance and fitness goals. The system can help a user correct form and enhance technique for a variety of sports/athletic and medical movements and activities, such as weight lifting, CrossFit, yoga, Pilates, karate, tai chi, boxing, mixed martial arts, Aikido, taekwondo, basketball, golf, tennis, baseball, bodybuilding, cricket, football, gymnastics, rowing, crew, lacrosse, hockey, field hockey, fencing, rugby, skiing, snowboarding, surfing, soccer, squash, swimming, tennis, volleyball, wrestling, diving, figure skating, ice skating, dancing, track and field, sprinting, throwing, jumping, long jumping, triple jumping, pole vaulting, discus, shot put, javelin, hammer, cycling, long distance running, triathlons, hurdling, table tennis, pool, darts, archery, badminton, horseback riding, horse racing, auto racing, physical therapy, rehabilitation from injuries, rehabilitation from surgeries and medial operations, healthcare applications, etc.

Exemplary versions can be applied and/or adapted for such other applications as video gaming, augmented reality, virtual reality, etc., to provide high accuracy devices able to track motion in simulated situations. For example, exemplary versions can be used with the Oculus Rift and other devices in augmented or virtual reality markets to provide new and novel experiences for the user by submerging them further into the simulated application. Moreover, personal trainers or coaching figures can enhance their training and coaching of users by basing efforts on more precise and accurate data. For example, a coach or personal training figure could use the training system for insights into the user's movements and to track the user's progress by evaluating patterns and trends. The system can also provide notifications (e.g., via text message, email, in-app and out-of-app messages, etc.) to highlight critical information related to the user's performance and progress. Data on user movement, performance, and progress during exercise, training, therapy, and rehabilitation can also be collected for anonymous big data analytics to gain insights into how athletes train, improve, heal, etc. These and other applications and markets benefit from valuable insight into the human body provided by the disclosed system.

In general terms and without limiting scope, exemplary versions of the invention will be discussed in the context of five main components, as outlined here.

(1) Garment: these include tops such as shirts, bottoms such as pants or shorts, accessories such as gloves, etc.

(2) Sensor Nodes: these typically house motion sensors and transmit unprocessed motion data to sensor modules and attach directly to the electrically conductive fabric of a garment. They serve as wearable personal sensing devices.

(3) Sensor Bands: these are sensors that share the same electrical componentry as the sensor node and the sensor module. These devices do not attach through the conductive fabric. These are particularly useful for users who prefer short sleeve shirts and shorts instead of long sleeves and pants. This component also serves as a personal sensing device.

(4) Sensor Module: typically, one garment (shirt, pants, etc.) has one sensor module, so an outfit having one shirt and one pair of pants would have two sensor modules, one for the "top," and one for the "bottom." This is typically the main processing unit that processes the sensor data and transmits wirelessly to a computing device that has a Graphical User Interface (GUI). They serve as a wearable personal sensing device.

(5) Electrically Conductive Fabric: this connects the sensor nodes to the sensor modules.

These components allow the system to capture full-body form motion of athletic and other movements, and send information wirelessly to a computing device with a GUI to give the user real-time feedback on movements. The motion sensors that are preferably used include a 3-axis accelerometer, 3-axis magnetometer, and 3-axis gyroscope (together, the accelerometer, magnetometer, and gyroscope, or AMG), coupled with data fusion algorithms, an extended Kalman filter (EKF), and an attitude heading and reference system (AHRS) to gather the raw data from the AMG and process it into movement orientation. The AMG is positioned to measure each major rigid limb of the body (arms, torso, and legs), for a total of (for example) 10 sensors in preferable versions. This provides full-body movement form measurement and analysis, not achieved by prior systems of comparable cost and mobility.

The "smart" garment/clothing include miniaturized motion sensors—such as, for example, microelectromechanical systems (MEMS) packages—that are integrated at multiple strategic positions in the clothing. The sensor node(s), sensor module(s), and electrically conductive fabric are sufficiently small such that the components provide an aesthetically pleasing, ergonomic, and unique user experience. Due to the size of the components, the fabric is very breathable and very stretchable, resulting in a very comfortable user experience. The electrical components and sensor integration into the garment are designed to withstand multiple machine wash and dry cycles. Exemplary methods (further discussed below) of integrating sensors and electrically conductive fabric into the garment methods (such as triple layering and sensor penetration) achieve both durability and comfort. Exemplary versions of the smart garment can be impervious to sweat and water.

Signal processing and error filtering techniques related to data fusion can be used in extracting orientation data from accelerometers, gyroscopes, and magnetometers. Software in the system enhances the sensor accuracy and reduces calibration routines, avoiding delays and unnecessary steps involved in receiving feedback from the product.

The training system can integrate video capturing capabilities into the architecture. The video capturing capability can be provided by the wireless-enabled mobile computing device with a camera, or any dedicated capturing device that is able to connect to the training system to transmit and receive tasks, services, commands, or a combination thereof. Video capturing capabilities would synchronize with motion and other data so as to provide additional information to the user, enhancing form analysis and feedback. Coupling biometric and motion data preferably invokes suitable external software tasks, processes, and services to provide the user with an ergonomic and easy to understand interface. The video may record in any frame rate which allows a user to understand the kinematics of human motion in the respective usage application.

A user can begin by wearing the garment(s) and starting to exercise, play sports, or otherwise move at (for example) a gym, outside in a field, under water in a pool or lake, at a clinic, or elsewhere. The exercise can involve (for example) weight lifting equipment (such as barbells, weight machines, dumbbells, kettle balls, or other free weights), balls, etc. The exercise can also involve other equipment, such as a baseball bat, a golf club, a javelin, a discus, a shotput, etc. Optionally, a ball, bat, club (or other equipment) can be equipped with its own motion sensor to allow for analysis of the equipment's motion simultaneously with analysis of the user's body motion. The end user would preferably use a wireless-enabled computing device, such as a smart phone or other suitable mobile computing device (such as a tablet, notebook, laptop, smart watch, etc.) with wireless communications technology (such as Wi-Fi, Bluetooth, etc.) for communicating with the circuitry of the garment and running application software. Networking capabilities (such as an internet connection or local/wide area network connections) can further be used to enhance post processing capabilities. The code related to user feedback can be stored and processed on the wireless-enabled computing device, or it can be stored and executed on a cloud server or remote stationary computing device, or it can be handled onboard the sensor modules, or any combination thereof. The user receives feedback regarding his or her motions, helping the user be more efficient and effective, and reducing the risk of injuries from improper form or technique.

The garment (or "smart" clothing) is preferably machine washable. The garment uses a combination of textile coatings, such as silicone, and highly stiff materials, such as polycarbonate and brass, to provide robust and structural bonds for protection from harmful contaminants which may damage sensitive electronic components. Sensitive components, such as electrically conductive yarns or materials and the electronic circuitry are protected against impact and also hermetically sealed through such coatings and bonding of highly stiff materials. The product form factor and care techniques are similar to compression athletic garment, like Under Armour or Lululemon compression offerings (for example, machine wash on cold and dry in dryer). The garments can also be washed by hand and hang dried for increased life. Standard washing solvents and household chemicals can be used to wash the garments, which are expected to last multiple machine wash and dry cycles.

Further advantages and features of the invention will be apparent from the remainder of this document in conjunction with the associated drawings.

DETAILED DESCRIPTION OF PREFERRED VERSIONS OF THE INVENTION

Figure 1:
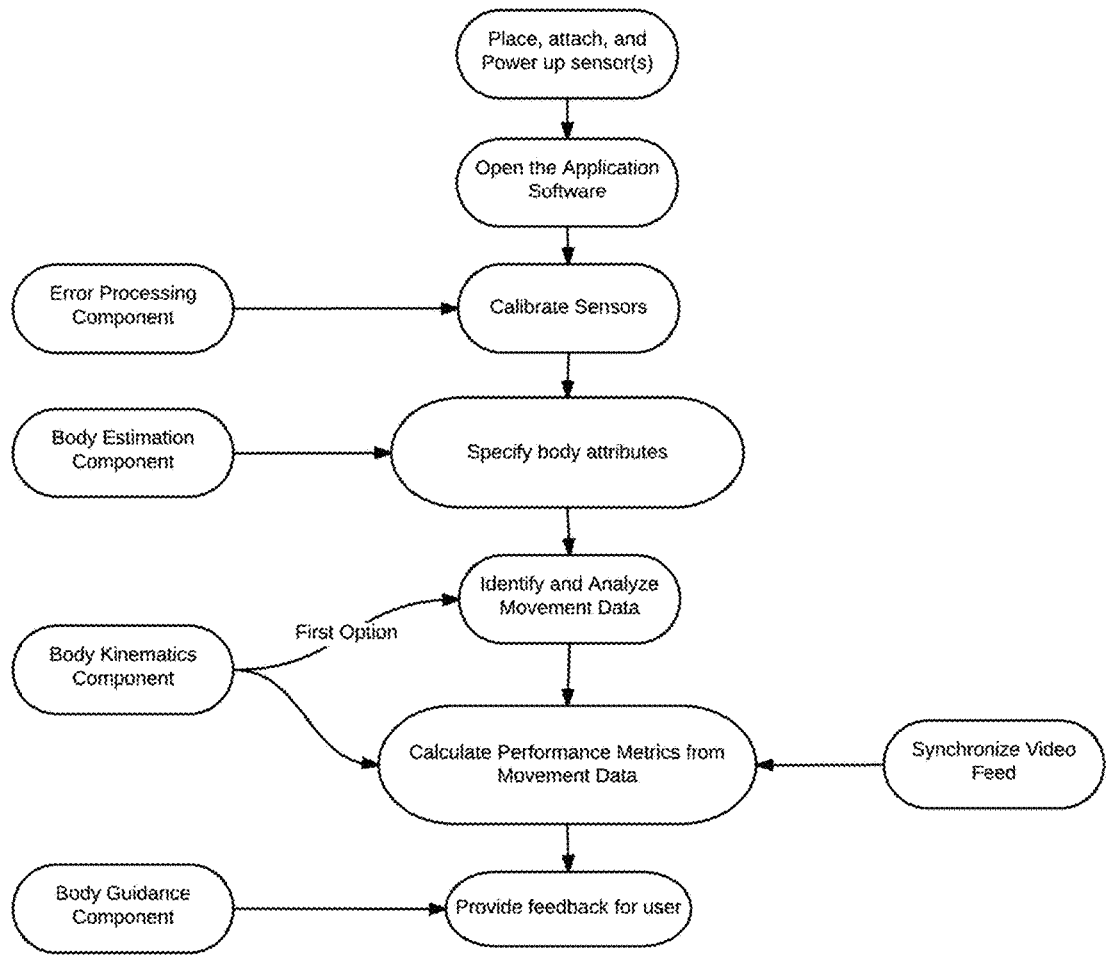
FIG. 1 represents an exemplary feedback process of exemplary training systems.

Referring initially to FIG. 1, an exemplary training system uses a variety of components and configurations to provide a method for characterizing, analyzing, and supplying a user real-time feedback on various performance metrics related to athletic and medical related movements. For example, at least some intelligent automated health and fitness analysis system(s) may be configured, designed, and/or operable to provide various different types of operations, functionalities, and/or features, such as one or more of the following: (i) automate calculation, detection, and input of data relating to exercise movement, such as (for example) repetitions, set completion, exercise completion, movement completion, range of motion, power, eccentric and concentric phase, balance, heart rate, caloric expenditure, tempo, acceleration, velocity, position, gamification score, form efficiency, rest time, distance traveled, force of impact, and 3D avatar movement; in addition to automating the process of using these data and services, the training system can also enable the combined use of several resources of data and services at once; (ii) automate the use of data and services available over the training system to determine and offer personal recommendations to a user to (for example, but not limited to) select a resistance load, perform a specified number of repetitions, adjust form and technique (post or during movement), etc.; (iii) enable the operation of components, tasks, and services to provide a GUI having, for example, charts, graphs, and animations to specifically display user performance metrics and offer personal recommendations. The user performance metrics can include, but are not limited to: set completion, exercise completion, movement completion, range of motion, power, eccentric and concentric phase, balance, heart rate, caloric expenditure, tempo, acceleration, velocity, position, gamification score, form efficiency, rest time, distance traveled, force of impact, and 3D avatar movement. At least a portion of the various types of functions, operations, actions, and/or other features provided by exemplary versions of the training system can be implemented at one or more client system(s), at one or more server system(s), and/or combinations thereof.

Body Guidance Component

A body guidance component is an automated and personalized workout mechanism to assist the user in attaining an athletic or medical related goal. The body guidance component compiles and prepares fitness or medical regimens relating to movements, including (for example) recommendations related to exercise or movement, resistance, repetition quantity, set quantity, movement plan, or a combination of thereof.

The body guidance component can include different types of components, modules, processes, systems, and the like, that may be implemented and/or instantiated using hardware and/or software. The different software and hardware components include, for example components related to: estimating and comparing state; using historical workout performance data; updating; database tracking; using a database library of athletic or medical movement; active input elicitation; using short and long term memory; storing data on a server; math modeling; machine learning modeling related to exercise repetition, set, and resistance load; using reference data; muscle affected by exercise modeling; orchestrating services; task flow modeling; service modeling; and output processing. Goal data can be collected from the user, and the component can compile and analyze historic data of (for example) kinematic movement to determine the progression status of the user with respect to the goal and to formulate the necessary movement regimen to achieve the goals. The user can continually update their body geometry to gain results.

The body guidance component categorizes goals into domains and matches movements based on pre-determined and assigned criteria and classifications based on how certain movements affect the body. For example, a user with a goal of gaining muscle mass in the chest segment of the body can utilize the body guidance component to formulate an exercise routine that focuses on exercises and methods of movement to target muscle activity in the chest segment. The body guidance component could formulate an interactive regimen involving, for example, athletic movements, quantity of repetitions, quantity of sets, quantity of resistance, with specifications on set completion, exercise completion, movement completion, range of motion, power, eccentric and concentric phase, balance, heart rate, caloric expenditure, tempo, acceleration, velocity, position, gamification score, form efficiency, rest time, distance traveled, force of impact, and 3D avatar movement, or a combination thereof. The body guidance component can continuously analyze and store performance data related to kinematics of motion, physiological measurements, or a combination thereof during a workout. The body guidance component could compare current status regarding user performance versus performance goals, such as (for example) the weight of the user or the maximum amount of weight which can be lifted. Using this information, the system can prescribe optimal movement regimens to attain goals in a quick and efficient manner. The historical kinematics of movement and physiological measurement data for each individual user can be stored within the cloud for subsequent access by the same or other devices for body guidance analysis, progression analysis, etc.

User Interface

The user interacts with the GUI of the application software to input necessary information about their body attributes and their goals. The user interface is responsible for communication of user input to software algorithms, and computation outputs to the user. User input includes, for example, athletic movement selection, closing of tasks, calibration of sensing devices, and initiation of the software. System outputs include, for example, notification messages, 3D videos of the exercise being performed (see FIG. 2), and performance metrics. The system can synchronize sensing devices, placed on one or more segments of the body, with the wireless-enabled computing device. The user can then select an exercise or body posture and perform a certain task. After the task is completed, the wireless-enabled computing device can provide feedback in different forms (such as visually through, for example, graphs and charts, and using sound such as through voice synthesis, etc.). The user is allowed to input information into the device and make selections relating to height and weight, body geometry, exercise, body posture, etc. These can be entered in any manner deemed suitable, such as through a touchscreen or using voice commands.

Connecting

The user wears garments and (if applicable) separate sensor bands and connects to the application software being run on the wireless-enabled computing device. As further discussed below, the user puts on garments so that sensor nodes and modules are worn in the correct position with respect to the human body. The user then opens the application software, which could be an application, executable, or software task depending on whether the wireless-enabled computing device is a smart phone, tablet (such as an iPad), laptop, or a desktop computer (such as an Apple computer, a Windows-based Personal Computer (PC), etc.). Once it is running, the software may automatically start searching for the garments and (if applicable) sensor bands to connect and synchronize a data transferring connection. The device which has the code base installed on its own electronic circuitry will start searching and scanning for recognizable systems through Wi-Fi, Bluetooth, internet, or other suitable connectivity protocols.

Garments (and sensor bands) may have unique radio addresses that are recognized by the application software, helping distinguish one person's system from another nearby person's system. This helps avoid or reduce interferences and confusion by allowing one user's system to recognize and communicate with the correct hardware. The unique radio addresses may be printed on the surface of the garment, case membrane, or otherwise made available to the user via (for example) email or other easily accessible and distinguishable method. The user could additionally or alternatively be provided with an "umbrella" code identifier which would query the cloud based server to automatically populate the unique device address list.

The sensor node(s), module(s), and sensor band(s) may have separate power buttons, or, in preferred versions, only the sensor module(s) and sensor band(s) have power buttons. Pressing a button migrates the sensors from a low power state, also known as a "sleep" state or "sleep mode," to a fully-functional state. Moreover, the sensor can migrate from a lower power state upon sensing movement. Once the power button is depressed, the sensor node(s), module(s), and band(s) begin to advertise their respective unique radio addresses for recognition by the computing device. Calibration preferably need only be performed once after initially wearing the garment(s) and sensor bands (if any) but before the user starts his or her first workout. Calibration is further discussed below. Additional calibration techniques for correcting positioning errors injected into the system during the alignment process are also discussed below.

Moving

Once the garment is connected to the software application, the user can select pre-defined exercises, athletic movements, workouts, etc., or create and perform their own exercises, movements, and workouts. The source code base for selecting workouts or for selecting or creating exercises can be executed on the computing device (with the GUI) or on a remote server, such as the cloud, or on-board the electronic circuitry of the sensor band(s), sensor node(s), or sensor module(s). The sensor module(s), sensor node(s), or sensor band(s) could also interface with the user to allow selection of exercises and navigation through the GUI. The user starts performing athletic movements, rehabilitation, or other suitable movements. To help the user progress, the system provides real-time feedback, examples of which follow.

(1) Voice Feedback: The wireless-enabled computing device informs and instructs the user regarding current performance and opportunities to improve on performance with respect to goals.

(2) 3D avatar Form Comparison: The computing device shows the movement of the user and/or idealized examples of movements using an avatar to instruct the user on how he or she may improve performance based on the movements performed and/or on the idealized movements.

(3) Multicolor Light: LEDs or electroluminescent fabric may be situated on each limb within electronic circuitry or electrically conductive fabric to illuminate and draw attention of the user to feedback, warnings, etc. as part of general informational notifications and guidance, and/or as part of alerts related to preventing injuries.

(4) Tactile Feedback: Vibration motors located in the garment(s) and (if applicable) the sensor bands can vibrate to indicate warnings of movement to prevent injuries and/or to provide general notifications.

(5) Push notifications: Notifications highlighting critical information related to the user's performance can also be provided via, for example, text message, e-mail notifications, in-app notifications, out-of-app notifications, social media responses, etc.

(6) Graphs and/or charts displayed on the screen of the wirelessly enabled device, providing indicators of user performance, such as set completion, exercise completion, movement completion, range of motion, power, eccentric and concentric phase, balance, heart rate, caloric expenditure, tempo, acceleration, velocity, position, gamification score, form efficiency, rest time, distance traveled, force of impact, 3D avatar movement, progression of performance over time, overall performance, or a combination thereof.

Sensor Calibration and Alignment

The sensor node(s) and module(s) should be properly aligned with respect to features of the human body to enhance accuracy and precision of the sensor readings. There may be alignment mark(s) integrated on or in the garment(s), which helps the user align the sensors properly. Alignment mark(s) can be placed on the sleeves of the arms, chest panel, back panel, shoulder panel, leg panels, and other places where it is important to indicate sensor position on the human body. Alignment mark(s) and features are further discussed below. Alignment instructions can also be visually indicated within the application software or within a user manual pamphlet that is included in the retail packaging. The position of the sensor node(s) and sensor module(s)—which may be integrated permanently into the base fabric of the garments—can be fixed relative to the alignment mark(s) of the garment(s). The position is set by angle and distance with respect to the alignment marks. Additional calibration techniques exist to correct positioning errors injected into the system during the alignment process (further discussed below).

Optionally, the system may include ankle or wrist sensor bands (to be worn like a typical watch or sports fitness band), gloves, and/or compression socks to be worn snuggly to the skin so as to limit relative motion between the device and the body. The sensor node(s) and module(s) are preferably positioned where there is a bony surface, as this impacts sensor accuracy. The motion sensors should preferably not be placed on a muscle. It is more effective to capture movement of the major bones of the human body because analyzing kinematics of human motion generally involves estimating the movement of the bone structure of the human body that results from muscle activity (rather than motion of muscles themselves). When the human muscle fibers contract (for example), the skin surface migrates. The AMG record movement of the sensor node(s), module(s), and/or band(s), and are agnostic to what causes the motion. With a bony surface, there is less chance of skin migration. It is noted that folding or rolling up a shirt sleeve or pant leg may also compromise accuracy and is preferably avoided. It is also noted that certain sensors may need to make contact with the skin to function properly, such as EMG, ECG, pulse oximetry, and HR sensors (further discussed below).

The garment(s) have a compression fit against the surface of the human body (i.e., be form fitting), such that there is minimal relative movement between the skin and the sensor nodes, the sensor module, and/or sensors in the wrist or ankle bands. Preferably the garment(s) provide a slight compression against the human body so as to press the sensor node(s) and sensor module(s) against the human body, reducing relative movement. The garments preferably exhibit a compression fit on the torso region, arm region, hip region, and leg region.

Garments should not be loose fitting or otherwise too large on the user's body.

In one method for calibrating the sensors, the user may assume a known pose and perform a quick predefined activity, such as (for example) jumping jacks or a randomized motion identified by the application software. This process can take under 10 seconds. This process should be done before a workout session or athletic activity is started, and should only be needed once after initially putting on garment(s) and (if applicable) sensor bands to acclimate the systems to the environment. Calibration is important because the relative position of the sensors change each time a person puts on the garment(s)/sensor band(s). Assuming a known pose aligns the assumptions of the application software and the actual position of the human body. One example of a known pose is the "T-pose" (see FIG. 6). The application software is designed to make assumptions on the position of the human body and it is the responsibility of the user to replicate the known positions. In this manner, the software can accurately extract position and align the movement of the sensors to the estimation of movement within the software. A known pose calibration helps correct/adjust for discrepancies between the intended sensor mounting location and the actual mounting location. This calibration can be done in any environment.

The system may also employ random motion calibration by requiring the user to do a series of jumping jacks or warm-up exercises to properly calibrate the sensors. These random movements and rotations may be used to acclimate the magnetometer component of the AMG to the magnetic fields in the intended workout location. This method can also be used to automatically identify the locations of the sensor module(s) in the strap model configuration(s).

Charging

A charging station can be provided for charging the sensor module(s), nodes, and band(s), either directly or indirectly. The batteries can be (for example) lithium polymer-ion batteries, or any other chemistry that allows the battery to be rechargeable. The charging station could also be used to charge wrist and ankle band(s), if included. Charging might require from 15 minutes to 4 hours, and the user may have to charge the sensor after (for example) 4 hours to 20 hours of continuous use. The charging station may charge battery sizes from 50 mAh to 1000 mAh. The electronic components may have low battery level indicators, preferably as LEDs placed on the circuitry to indicate battery charge level.

Feedback

The user receives a combination of real-time feedback and post-athletic movement feedback. This is useful for new athletes as well as veteran athletes. Regular and accurate feedback on performance can help an athlete train more optimally, create awareness to prevent injuries, recover from previous injuries, and reach desired performance goals. Real-time feedback is provided during an exercise or athletic movement. Post-exercise feedback is provided after an exercise or athletic movement is completed, for review during a rest period or whenever there is downtime. The user interface can mimic actual feedback that a live personal trainer, coach, therapist, or doctor would administer (if only to enhance usability), but the system's feedback is generally more accurate and possibly more conclusive and useful. The user can receive feedback or information from the system through visual cues, audio, and vibration in real-time or at a later time based on system settings, or a combination thereof.

Figure 2:
FIG. 2 is an exemplary virtual representation of a human for displaying ideal movement, technique, and/or posture for emulation by a user.

The computing device can display, for example, a virtual representation of a human that demonstrates ideal movement, technique, and/or posture for the user to emulate, as shown in FIG. 2. A graphical display like the one in FIG. 2 can be used to showcase the optimal versus the actual movement of the user to assist the user in making adjustments to reach optimal form and technique. Methods of providing guidance and feedback on corrections to be made to movements include, for example, color coding of body segments or vector lines representing correct vs incorrect form factor. In this manner, the user can manipulate his or her body to achieve goals more quickly in an easy to understand and effective way. Graphs and/or charts can be used to provide indicators of user performance, such as (for example) set completion, exercise completion, movement completion, range of motion, power, eccentric and concentric phase, balance, heart rate, caloric expenditure, tempo, acceleration, velocity, position, gamification score, form efficiency, rest time, distance traveled, force of impact, 3D avatar movement, progression of performance over time, or a combination thereof.

Real-time feedback is processed and given by (for instance) a wireless-enabled computing device, such as a smart phone, or a stationary computing device, such as desktop personal computing device. Examples of feedback provided are discussed below.

(1) Voice feedback: Using, for example, an integrated speaker system, a headphone, or an external audio system that connects with the computing device, the system can use a voice to speak to the user. The code base for voice feedback can use (for example) natural language processing (NLP). Many operating systems, such as those offered by Android or Apple, have built in APIs (application programming interfaces) that offer easily accessible and free-to-use software components to integrate voice feedback into the application software. Typically, this computation is performed on-board the wireless-enabled computing device. The computations may also take place on a server that is remote from the mobile or static personal computing device(s). More details on types of voice feedback metrics are provided below.

(2) Visual Feedback: (i) Charts and graphs can be a succinct and effective way to provide feedback. While the user is exercising or performing an athletic movement, it is important to provide information that is not distracting and can be easily understood within the time frame of a quick glance at the GUI. More details on types of charts and graphs feedback metrics are provided below. (ii) 3D avatar movements can provide, for example, replays of prior movements, and can allow for the ability to pan and rotate around the 3D avatar to further study movement. This can be a very effective communication tool to easily communicate the quality of movement and to provide guidance to improve movement. This can be essential in helping a user prevent injuries and achieve their performance goals by critiquing a user's performance and analyzing weaknesses to iteratively improve upon the movement. This also enables ghost movement comparison (i.e., comparing current movement (for example) to past movement, or (as another example) to an idealized version of the movement). The ability to compare movement with a validated and optimal movement in a visual manner can be a very effective communication tool to users. Often, a user's form suffers during athletic movements or exercises. Having a simplistic representation can provide a very effective and easy to understand correction platform for a sufficiently complex problem. (iii) Light feedback: the garment(s) preferably contain lights in the fabric or sensor circuitry (sensor node(s), sensor module(s), and band(s)) where multi-color LEDs or multi-color electroluminescent lights or fabric may help indicate performance metrics. Lights may be used for injury prevention and general notifications and alerts about performance or otherwise.

(3) Tactile feedback: Vibration motors affixed to the garment(s), sensor node(s), sensor module(s), or band(s) may emit, for example, a 0.4 to 800 Hz (frequency) vibration for 50 ms to 200 ms (time). Vibration may be used for injury prevention and general notifications about performance or otherwise.

Post athletic feedback may be processed and given from a wireless-enabled computing device, such as a smart phone, or from a stationary platform, like a desktop computer. The code base for visual feedback may be included on the wireless-enabled computing device. Many operating systems, such as offered by Android or Apple, have built in APIs that offer easily accessible and free to use software components to integrate charting and graphic tools into the application software. The computations may also take place on a server that is remote from the mobile or static personal computing device(s). More detailed graphs and charts can be used to communicate progress over time. In some applications, detailed progress is essential and in other areas, smaller amounts of information are needed. Post-exercise feedback metrics are further discussed below. Using 3D avatar movement, users can compare their movements with a 3D representation within the GUI of the application software. This visual representation may help the user determine and identify areas for improvement. The 3D avatar can help coach the user and it may bring an exciting user interface experience to the user.

Usefulness of Feedback to the User (1) Reaching Goals Faster and Safer: Feedback that a user can easily understand and articulate allows the user to adjust movements and change performance with relatively little downtime. The system thus aims to provide information and exercise data that are actionable and contextual to help the user achieve his or her desired performance goals sooner, reduce injuries, etc. This type of feedback can be easily custom tailored to any application where movement form is the key to success.

(2) Calculations: These metrics and more could be calculated on the sensor module(s), but preferably are calculated on-board the wireless-enabled computing device, server, or stationary application where there is possibly an abundance of computational resources.

(3) Competition: The resulting metrics can provide an appealing and competitive user experience. The user may, for example, publish metrics on social media platforms, such as Facebook, Twitter, Instagram, etc., to compete with friends and family. The user can also compare results to others through the software user interface itself.

(4) Data Aggregation and Reporting: The resulting metrics can be aggregated into one user interface for a coach, trainer, therapist, doctor, team, exercise class, or other groups of people who train together, at the same venue, perform the same exercises, or otherwise wish to view each other's metrics. This is useful (for example) for a coach to be able to view metrics and progress for multiple users at once in one software interface. This enables the coach and the users to see each other's progress, compete with each other, and compare performance to each other.

(5) Use Cases: The following metrics can be presented in real-time (during the exercise or athletic movement) or post exercise or athletic movement. They may be presented in various formats, such as graphs and charts or via voice feedback. The list of feedback mechanisms below is an example of how many metrics can be calculated, but is not intended to limit the metrics as they may vary depending on the athletic movement application.

(i) Repetition Counting

A significant pain point when exercising or performing athletic movements (if applicable) is to keep track of repetitions and sets completed. Values are often forgotten or not tracked properly. The application software can keep track of repetitions, as well as the magnitude of repetitions and sets, to provide performance progress analysis and feedback. Without automatic repetition counting, the user would have to enter each repetition, and that can easily create an unappealing user experience and potentially make it less likely a user will continue to work towards his or her goals.

Repetitions can be calculated through, for example, machine learning techniques, such as gathering many data samples and analyzing the pattern and identifying trends in real-time. Other methods include looking at the orientation and the sequence of orientation of all or a specific set of (focused on a specific exercise or athletic movement) limbs to set thresholds and identify patterns that qualify as a completed repetition. Other methods include, but are not limited to, looking at joint angle between limbs and establishing thresholds and patterns that count as a completed repetition, or identifying inflections in limb angle rates. This is one approach, however, as repetition counting can be determined using other methods.

(ii) Completion of Exercises, Sets, and Movements

By virtue of the repetition counting, orientation recognition, and machine learning techniques, the application software can recognize when the user has satisfactorily completed the desired exercise, set, or movement. For example, in a bench press, the application can recognize when the user has lowered the bar all the way to his/her chest, and extended the arms fully toward the sky to complete the movement. As another example, the application can recognize whether the body angle has appropriately entered an "inverted V" to be sufficient to be classified as a "downward dog" in yoga.

(iii) Range of Motion (ROM)

ROM is related to injury prevention and maximizing benefits of exercise routines. If range of motion begins to decrease as the user completes repetitions and more sets, the user may be getting fatigued, which in turn increases the likelihood of an injury. The ROM metric is also important for enhancing the effectiveness of exercise routines, and discouraging short cuts during exercises. ROM can be calculated using an algebraic method, by looking at the orientation of the limbs and using trigonometry and forward or inverse kinematics to track a specific point on the body. By analyzing the path and trajectory, it is possible to determine the ROM. This is one approach, however, as ROM can be determined using other methods.

(iv) Power

Power is related to the amount of effort that goes into each repetition and set, and is a fundamental metric for certain exercises and athletic movements. Power can be used (for instance) to assess the likelihood of an injury as the power generated by a user decreases with more repetitions. The pattern and trends of power related to athletic movements can provide insights into the human body. Power calculations generally include determining work divided by time. Time can be tracked within the application software with respect to orientation. Work can be determined by the product of mass lifted (body weight of limbs added with weight of resistance) and distance. Using the graphical user interface (GUI) of the application software, the user can enter his or her weight as well as the weight of the objects to be lifted. Distance can also be calculated algebraically, in a similar fashion as for the ROM.

(v) Eccentric Phase and Concentric Phase

These metrics are particularly relevant to rigid motions, such as weight lifts. When the muscle lengthens, this is the eccentric phase, and when a muscle shortens, this is the concentric phase. For example, in a bench press, the downward motion is the eccentric phase and the upward motion is the concentric phase. Monitoring eccentric and concentric phases can be useful for evaluating form efficiency and enhancing muscle development. These can be determined by analyzing the displacement with respect to time of certain body parts, and monitoring kinematics of specific limbs. Typically, the time component is the duration of the downward or upward stroke. This is one approach, however, as eccentric phase and concentric phase can be determined using other methods.

(vi) Balance

It is useful to determine whether the user is inadvertently favoring a portion of the body, such as by identifying if a user is exercising the left bicep more than his or her right side. This metric is also useful in assessing stability with such exercises as Yoga. This is one approach, however, as balance can be determined using other methods.

(vii) Heart Rate

Heart rate is useful for maintaining health and measuring performance in many applications. It can also be used as an input to calculate caloric expenditure and overall performance.

(viii) Caloric Expenditure

Also referred to as calories burned, this metric is useful in maintaining weight and tailoring diets, as well as for selecting and changing workout regimen. Estimating caloric expenditure involves such variables as user height, gender, age, and body weight. Different methods for calculating caloric expenditure are available, with varying levels of accuracy and precision. However, based on movement and activity level, power calculations and basal metabolic rate estimates are additional ways of determining caloric expenditure.

(ix) Tempo (Frequency)

Consistency of movement is important for athletes as they train to replicate movements with precision. Tempo, which is not relevant to all movements, affects muscle groups differently. For example, moving slowly can affect the slow twitch muscle fibers, and fast movements can train and focus on fast twitch movements. Tempo is thus an important metric for users wishing to focus on training particular muscle fibers. Tempo can be calculated using, for example, the frequency of repetitions over time and an analysis of range of motion. This is one approach, however, as tempo can be determined using other methods.

(x) Acceleration

Acceleration is important for users in many applications. Acceleration is the change in velocity, so it measures how the user is affecting the velocity at which the movement is being performed. Changes in acceleration can be an indicator of better or worse athletic performance, and can also be an indicator of likelihood of injuries.

(xi) Velocity

Velocity is important for users in many applications. Velocity is the change in position, so it measures how quickly the user is performing the exercise. Changes in velocity can be an indicator of better or worse athletic performance, and can also be an indicator of likelihood of injuries. Examples where velocity is of paramount importance include a baseball swing and a baseball pitching motion.

(xii) Position

Position is important for users in many applications. In many repetitive exercises and movements, the user should be in the same position before, during, and after the exercise. Position refers to the precise location in 3-dimensional space of every joint on the body, and the relative positions between those joints. The difference between being in the optimal and suboptimal position can be the difference between a good and poor performance. Being in the incorrect position can increase the likelihood of injuries. Examples where position is of paramount importance are many full-body weightlifting exercises, such as a squat, deadlift, and power clean.

(xiii) Gamification Score

Video games can be entertaining, and the use of "scores" (a unit-less measure) can be a motivator. This can be applied to fitness to generate excitement and competitiveness. Users can compare their game-like scores, which are representative of performance and progress, with those of other users. Because such metrics as power and total weight lifted are specific to an individual user, they cannot readily be compared with (for instance) the values for a user of another gender and age (because the comparisons are so fundamentally different). However, using a normalized score system based on select variables, such as gender, body weight, etc., the exercises can be gamified with respect to users in other demographic groups as well. This is one approach, however, as gamification score can be determined using other methods.

(xiv) Form Efficiency (FE)

Consistency can be important to a user's success as an athlete. A FE metric can be based on, for example, orientations of several limbs and specific trajectory of the human body. A user (for instance) can improve on golf swings, baseball pitches, basketball throws, weight lifting movements, etc., by enhancing consistency. FE could be calculated by comparing a trajectory of actual movement relative to ideal movement. Ideal movement can be based upon, including, but not limited to, the user's body geometry, age, gender, athletic movement, and more. FE units can be in percentage, taken by analyzing the difference between the ideal versus actual movement in a specified time. Many assumptions can be taken to determine the difference in trajectories. The software could identify the upper and lower bounds of the trajectory of movement to identify levels of curve fit. From these levels of curve fit, FE could be established based on the bounds established. This is one approach, however, as FE can be determined using other methods.

(xv) Rest Time

In some applications, users perform exercises and rest in between sets of the exercise. One measure of the efficiency and effectiveness of training is the rest time between sets. The software interface can measure the time in between sets and report back to the user. By integrating the measure of rest time with other metrics and tracking progress over time, the software can enable users to identify how adjusting their rest time could affect performance.

(xvi) Distance Traveled

In some applications, users perform exercises where one of the metrics is overall distance traveled. Examples include running, cycling, and swimming. The software interface measures the distance traveled and reports back to the user. By integrating the measure of distance traveled with other metrics and tracking progress over time, the software can enable users to identify how to improve their distance traveled.

(xvii) Force of Impact

In some applications, the force of impact relates to the likelihood of injuries. For example, in football and hockey, the force and directionality of impact during collisions can relate to the likelihood of concussions. As another example, in running and jumping, the force and directionality of impact of the user's foot striking the ground can relate to acute and chronic lower body injuries. The software interface measures the force of impact in three dimensions over time and reports back to the user. The software interface can give real-time alerts to users, coaches, trainers, therapists, and doctors on force of impact. Machine learning algorithms can relate the force of impact to the likelihood of injuries.

(xviii) 3D Avatar Movement

In helping users identify and improve quality of movement to prevent injuries and maximize benefits of time spent, motion sensor output is coupled with data fusion algorithms to feed real-time form data to a processing unit for rendering and illustrating a 3-dimensional human avatar that mimics the movements of the user. The ability to visualize performance adds depth to the fitness experience, providing an insightful tool to help coach and guide a user to improve performance. The 3D avatar can be used in at least two ways: comparison and replay.

Replay refers to the ability to pan and rotate around a 3D avatar to further study movement. It can be important to help users identify areas of improvement and visualize how they can improve. Panning and rotating presents new vantage points for the user. Moreover, the ability to repeatedly replay movements helps the process of analyzing, processing, and understanding the information.

Regarding comparison, there are various ways to communicate how to improve an athletic movement or provide guidance to move in a different method. For instance, the 3D avatar can have a ghost 3D avatar superimposed directly on top of the user's 3D avatar. The superimposed avatar can represent, for example, a gold standard for particular movements. Moreover, the superimposed 3D avatar can take the form of a famous or recognizable figure, such as (for example) a professional athlete, or their friend and family, for a more exciting and appealing user experience. Explicitly showing the user how to move or improve visually can make it easier for the user to reach desired performance goals.

The 3D avatar can be implemented, in part, using open source platforms—like Unity and Unreal game engines made by Epic Games, and CryEngine made by Cryteck—which are traditionally used by game developers. Such a component could provide the base calculations for the 3D avatar and human skeleton. To activate and move the 3D skeleton, the system can use various software components working in harmony: a signal processing component (discussed later), a body estimation component, and a body kinematics component.

The second component (i.e., the body estimation component) is executed every time a new determination of body height or weight is established. This component is executed early in the user configuration process to learn about the user and generate data used to calculate specific human body kinematic information and feedback data. This component can be part of the source code as an object for which data can be input, processed, and output for use by other components.

For analysis of the kinematics of human motion, the system can identify the human body having multiple segments, joined together to form a system of chains and linkages. The segments can include, for example, the forearm, upper arm, thigh, shank, foot, head and neck, upper trunk, middle trunk, lower trunk, and fingers. Based on a user's input of body height and weight, the segment mass, moment of inertia, and center of mass of each linkage can be estimated. The user may also input the lengths, circumferences, masses, and/or other measurements of each segment of his/her body. The length and cross section of each segment is estimated to render segment mass. The joint degree of freedom can range from one to three degrees of freedom, depending on the specific joint.

The user can also input into the application whether or not specific parts of his/her body are sore, fatigued, strained, or otherwise injured. The user can also input other information that relates to his/her lifestyle, training, and exercise, such as: information on sleep, information of food and water consumption, mood, stress level, etc. The app can also integrate with other applications to collect and share data that relates to the user's lifestyle, training, and exercise.

The body estimation component may involve multiple different types of components, modules, processes, systems, and the like. For example, the training system may include one or more of: estimated state component(s); update processing component(s); active input elicitation component(s); short term memory component(s); long-term memory component(s); math model component(s); reference data component(s); cloud computation component(s); services orchestration component(s); task flow models component(s); service models component(s); and/or output processor component(s).

The body estimation component, which can be part of system software, receives body geometry as an input from the user. Body geometry information can be transmitted through the processing circuitry and stored in a database. The user may subsequently be allowed to alter the body geometry relating to the body height and weight to modify the estimation of the body algorithm. In this manner, the data processed from the body estimation component is manipulated to be passed to other components, tasks, services, and so on to unify the elements of the training system. The body estimation component can allow other elements of the training system to calculate and make recommendations to complete the method to characterize, analyze, and supply feedback to a user relating to human kinematics.

The third component (the body kinematics component) defines the orientation and the position of human body segments and joints. The body kinematics component identifies the user's actual movement through bio-information collected from one or more personal sensing device(s).

Related kinematic data includes, but is not limited to, range of motion, power output, optimal movement, repetition counting, movement evaluation, and velocity. This component can also be implemented as part of the system's software as an object for which data can be input, processed, and output for use by other components. The component calls processed data relating to the human body geometry and personal sensing device physiological data. This component is executed every time a user wishes to analyze a body posture, medical related movement, or athletic movement. This task may or may not be conducted simultaneously when a user is performing exercise movement or posture.

The body kinematics component may include different types of components, modules, processes, systems, and the like, that may be implemented and/or instantiated using hardware and/or combinations of hardware and software. For example, the training system may include: one or more simultaneous active signal processing component(s); estimated state component(s); comparison state component(s); inverse kinematic model component(s); update processing component(s); time step tracking component(s); active input elicitation component(s); short term memory component(s); long-term memory component(s); math model component(s); reference data component(s); data compensation model component(s); Cloud computation component(s); services orchestration component(s); task flow models component(s); service models component(s); output end effector position component(s); and/or output processor component(s).

The body kinematics component work flow begins as the personal sensing device begins to transmit signals. This component can receive input data relating to segment movement measurements, temperature measurements, ECG measurements, EMG measurements, pulse-oximetry or a combination thereof. The rotation rate and angular orientation information is calculated for each respective body segment, for which processed data includes, but is not limited to, segment orientation, relative segment position, joint position, and relative joint position. The output data is directed to kinematic analysis algorithms that use forward kinematics and joint constraints to calculate translation position and rotation of the body end-effector.

The body kinematics component may have the ability to recognize movement automatically, as the component may contain domains, tasks, and services which analyze movement data from one or more personal sensing device(s). Based upon each characterization of movement, the corresponding movement corresponds to a designated kinematic movement path. In this manner, the data processed from the body estimation component renders an output to be passed to other components, tasks, services, and so on to unify the elements of the training system. The body estimation component can allow other elements of the training system to calculate and make recommendations to complete the method to characterize, analyze, and supply feedback to a user relating to human kinematics.

Signal Processing

The signal processing algorithm preferably includes error handling capabilities to compensate for external disturbances injected into the system through dynamic motion events and/or environmental effects.

(1) Dynamic Magnetic Disturbance Compensation

Figure 3:
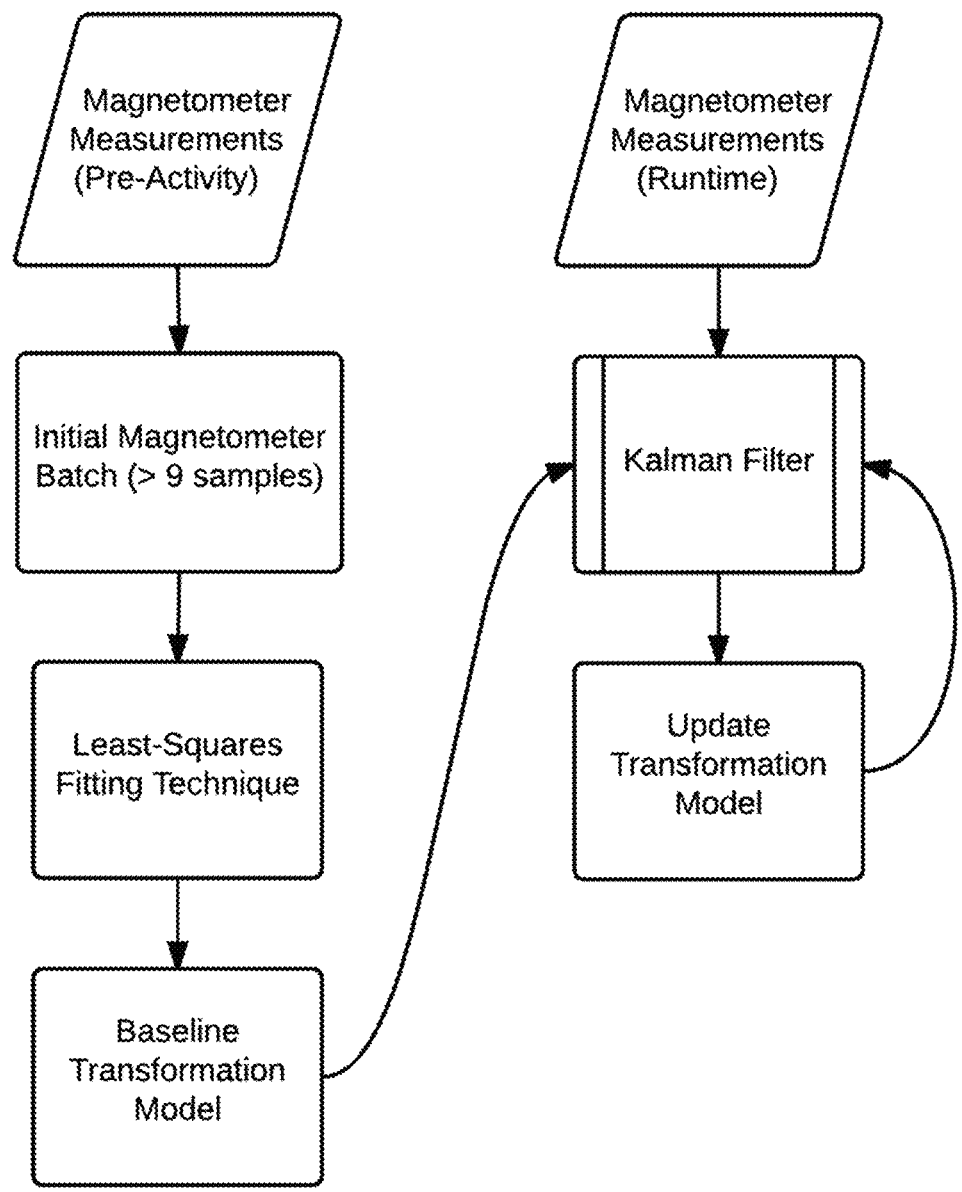
FIG. 3 represents an exemplary magnetic field disturbance compensation technique involving an extended Kalman filter and magnetometer channel measurements.

This method uses a recursive least squares fitting algorithm to dynamically compensate for hard-iron and soft-iron disturbances. The process uses (for example) an initial batch of magnetometer readings (greater than nine samples) to define an ellipsoid. Knowing a fixed magnitude vector should circumscribe a sphere under random rotation, the parameters of the resultant ellipsoid not representative of a sphere can be used to transform the raw magnetometer readings into a fixed magnitude corrected frame. The transformation properties are continually recalculated and updated as new magnetometer samples are received to get its recursive nature. The process is represented in FIG. 3 (related to magnetic field disturbance compensation).

(2) Adaptive Measurement Error Matrix.

Figure 4:
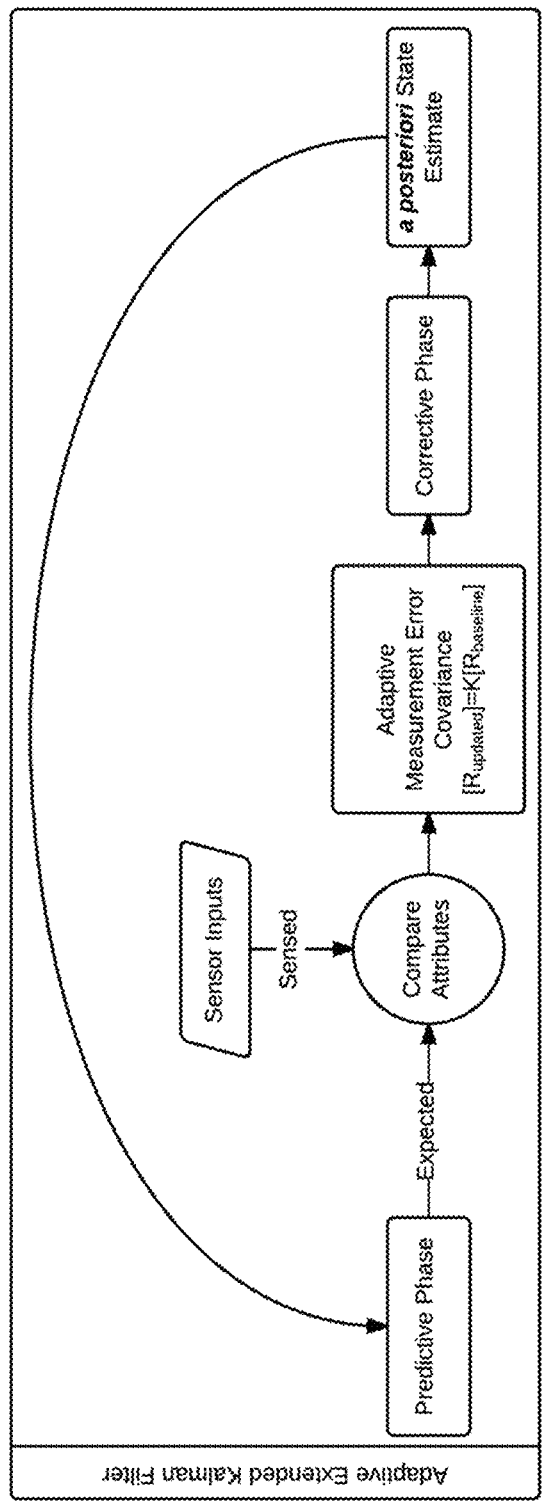
FIG. 4 is an exemplary adaptive extended Kalman filter process.

This method uses attributes of the sensor measurements to adapt the elements of the measurement error covariance matrix of the extended Kalman filter correction phase during runtime. This modification directly influences the effectiveness of the corrective phase of the Extended Kalman Filter. When in an undesirable condition such that the accelerometer and/or magnetometer are reporting values outside expected ranges, the algorithm can discredit the contribution of the accelerometer and/or magnetometer and rely more predominately on the gyroscope to maintain attitude state estimation until the disturbance subsides. The sensor attributes used in this method include, but are not limited to, magnitude of accelerometer channels, magnitude of magnetometer channels, and magnetic inclination angle derived from the current state estimation of the extended Kalman filter and the magnetometer channel measurements. The process is represented in FIG. 4 (related to an adaptive extended Kalman filter process). The method uses a continuous adaptive function, such as (for example) an exponential decay function. Alternatively or additionally, the method uses a piecewise function dependent on the sensor measurement attributes and pre-defined thresholds. Coupled with data fusion algorithms, the Kalman filters and the attitude heading and reference system gather raw data from the AMG and process it into movement orientation.

The firmware—which is generally a type of software that is stored on read-only memory of (in this case) the System-on-Chip's microprocessor (which is part of the electronic circuitry)—provides the ability for the microprocessor to connect and transmit information to and from several electrical components, such as the sensors, buttons, etc. Algorithms, software tasks, software services, and many more routines can be stored within the firmware. There are a variety of languages that can make up the firmware. For instance, C, C++, Java, and many other languages are capable of expressing the algorithms, services, and tasks. The sensor module(s) can connect directly and collect unprocessed data from the sensor node(s) and (in some versions) the sensor band(s). The following computations can include, but are not limited to, signal processing, compensations, filtering, and error handling capabilities.

Figure 5:
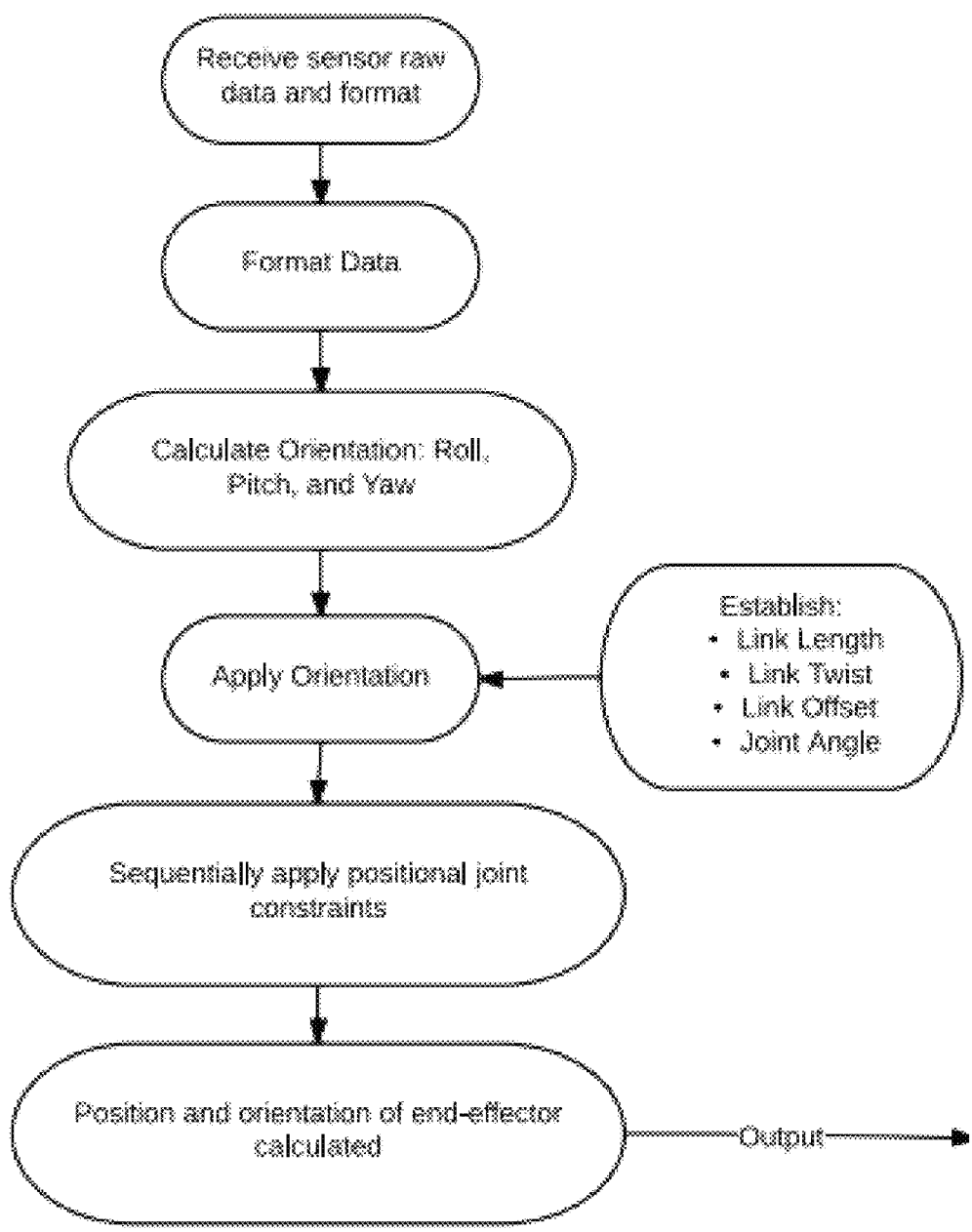
FIG. 5 is an exemplary flowchart for data processing.

A signal processing engine component removes sensor noise and covariance from unprocessed data collected by various physiological sensors within the personal sensing device circuitry. The signal processing engine component characterizes, filters, models, integrates, estimates, predicts, formats, reformats, compensates variables with reference data, derives, and stores data in long and short term memory from one or more personal sensing devices. The component and all combinations of tasks and services can be part of the software infrastructure as one or more object(s) for which data can be input, processed, and output for use by other algorithms. An exemplary flow chart can be seen in FIG. 5.

The signal processing engine component may include different types of components, devices, modules, processes, systems, and the like, which, for example, may be implemented and/or instantiated via the use of hardware and/or combinations of hardware and software. For example, the training system may include one or more of the following types of systems, components, devices, processes, and the like (or combinations of thereof): one or more simultaneous active signal processing component(s); estimated state component(s); variance or uncertainty of the estimate component(s); update processing component(s); time step tracking component(s); active input elicitation component(s); short term memory component(s); long-term memory component(s); math model component(s); reference data component(s); data compensation model component(s); services orchestration component(s); task flow models component(s); service models component(s); Cloud computation component(s); output processor component(s).

The signal processing engine component may use services to collect data in real time or in a calculated delayed time step from one or more personal sensing device(s). In variations of the system, the signal processing engine component can use orientation data to represent absolute orientation of a user's kinematic movement. This engine component can eliminate or reduce noise and reduce the effects of sensor drift. It can also interact with sensors including, but not limited to, one or more accelerometer(s), gyroscope(s), magnetometer(s), temperature sensor(s), electromyography sensor(s), electrocardiogram(s), pulse oximetry(s), or a combination of thereof.

The signal processing engine component can be designed to have a recursive nature, allowing real-time analysis or a calculated delayed time step of one or up to several personal sensing device(s) using several different types of components, devices, modules, processes, systems, and the like, or a combination of thereof, to produce statistically optimal estimates, a combination of multiple-stage processes to eliminate (for example) uncertainty in measurement, random noise, and covariance data for an outcome of minimized covariance, error, and randomized noise.

In this manner, the data processed from one or more personal sensing devices can be manipulated to minimize covariance and error for high accuracy and precision of calculated metrics, implemented tasks, and services for a combination of different types of components, devices, modules, processes, systems, and the like. The data processing engine component unifies elements of various components in the training system.

Garment

Figure 6:
FIG. 6 shows an exemplary avatar in a "T pose" position.
Figure 7:
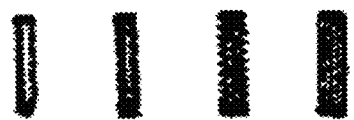
FIG. 7 shows exemplary button hole examples.

The garment is an interaction platform for the user. The garment guides proper alignment of the sensor node(s) and the sensor module(s) on the user's body. Alignment marks or features placed on the garment(s) can be, for example, visual indicators that are screen printed, sewn, embroidered, or otherwise. These indicators could point to a specific orientation that the sensors should abide by. The seams could be used as alignment marks; they could indicate to the user (for example) that the sensors should be facing in a certain direction and at a given angle to be in line with a limb when the user is in a T pose (FIG. 6). There could also be cutouts or apertures for the thumb or elbows or other limbs to guide the user to wear the garment(s) properly. The user would place their limbs through the cutouts for proper alignment of the garments. These cutouts or voids would be specifically aligned with the sensor node(s) or the module(s), so that when the user adjusts the clothing, the sensor node(s) or the module(s) are dragged along to land in the correct position. Sensor voids can be slots, holes, or a variant of the aforementioned shapes which is placed on the base fabric of the garment. It may occupy a cross sectional area of up to 490 squared millimeters. The sewing pattern and geometry can be similar to that used for buttons (FIG. 7).

All sensor nodes, electrically conductive fabric, and sensor modules can be housed by or otherwise secured to the garment. The sensor node(s) may be permanently integrated, woven, or adhered to the garment(s). The sensor module(s) may be permanently integrated, woven, or adhered to the garment(s), or may be removable. The electrically conductive fabric is permanently integrated into the garment(s). To enhance comfort (which can enhance usability as well as effectiveness), the garment may be provided with sweat wicking properties, anti-microbial properties, and be designed to increase blood circulation, prevent injuries, etc. The garment may have sensor voids placed on the surface of the base fabric for the sensor node casing membrane to pass through for attachment to the garment, electrically conductive fabric, and other components that make up the electrically conductive fabric.

The garments can (for example) include: a long sleeve shirt and pants; a short sleeve shirt and pants, along left and right wrist sensors/bands; a short sleeve shirt and shorts, along with left and right ankle sensors; a short sleeve shirt and shorts, along with left and right ankle sensors as well as left and right wrist sensors. Additionally, the system can affix sensors to other body parts of interest including head, neck, lower-back, etc. The system can also include one or more sensors secured to weight lifting equipment, a ball appropriate for a sport, or an external object that is appropriate to track orientation, position, or distance.

Regarding materials, the garment can be made from a highly elastic, breathable, lightweight synthetic blend of materials, such as nylon, Lycra, polyester, natural fibers, a suitable combination of natural and synthetic fibers, or spandex, to provide a compression fit against the human body to properly attach the sensors and gather movement data of the user. The garment provides compression fitting to promote minimal relative movement between the motion sensors and the user's body. The garment could be made in varying sizes to accommodate any user, from children's sizes to adult males and females. The garment could use standard practices and techniques commonly used to construct compression fit clothing. The garments could be available in a myriad of colors.

Sensor Nodes

The sensor nodes are designed to allow the garment(s) to be capable of withstanding multiple machine washing and drying cycles and harsh conditions during exercising, while collecting accurate sensor measurements in a cost effective way. There are two primary components that make the sensor node: the case membrane and the electronic circuitry. The case membrane houses and protects the electronic circuitry and provides physical alignment features to hold the sensitive electronic circuitry in place to make it possible for the garment(s) to record accurate and precise measurements. It also interacts with the electrically conductive fabric in a unique and robust manner to enable the system to withstand machine washing and drying cycles. The electronic circuitry itself can use industry standard manufacturing techniques for sensory and electronic components that are packaged to fit within the case membrane.

There may preferably be four sensor nodes permanently attached on each garment (for example a shirt or pants) that can be directly connected to one sensor module via electrically conductive fabric. In such a version, two sensor nodes can be connected in series, and another pair of sensor nodes can be connected in series. Together, each pair of sensor nodes could be connected in parallel to the sensor module.

A sensor node is placed on: left and right wrists or left and right mid-forearm; left and right upper arms; torso; hip; left and right thighs; left and right shins; left and right hands (which could include all fingers and palms); left and right feet; and head.

Case Membrane

Figure 8:
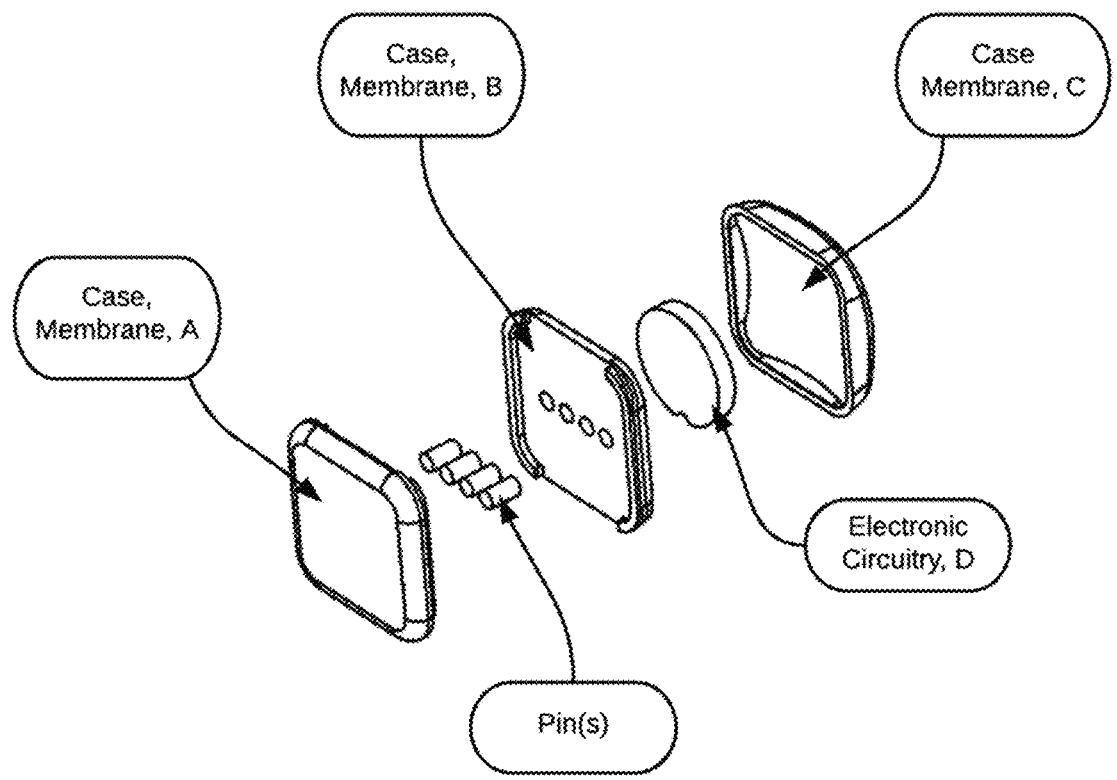
FIG. 8 shows a sensor node case membrane.

The sensor node includes a three-piece case membrane (FIG. 8):

Part A: This part is permanently attached onto the garment in the final stages of assembly. The purpose is to secure the assembled Part B and C (discussed below) onto the garment and to provide alignment and protection for the electrically conductive fabric, the pin(s), and the garment.

Figure 35:
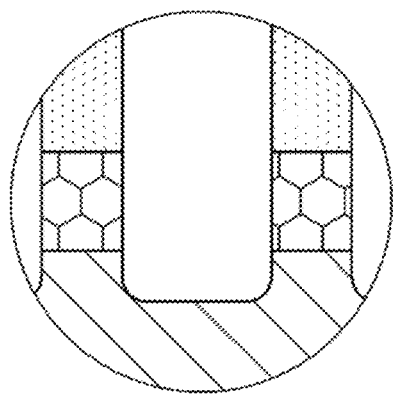
FIG. 35 depicts an exemplary sensor node or exemplary sensor module installed in an electrically conductive fabric.
Figure 35:
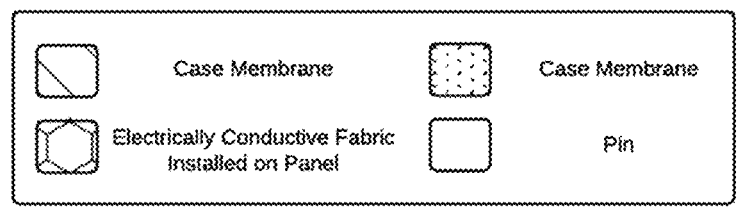

Part B: This part is permanently attached onto the garment in the final stages of assembly. This part is designed to hold the pin(s) and provide alignment geometry to hold the electronic circuitry. Part B interacts directly with the garment and the conductive fabric. It features one or more pin(s) which directly penetrate and interact with the conductive fabric (FIG. 35).

Part C: This part features a void complete with alignment features to hold the electronic circuitry. Part C is adhered to Part B once the electronic circuitry is mounted into Part C. It provides protection to the circuitry against impact forces such as drops of more than 90 g. It also provides protection to the circuitry and all other supporting electrical components against dirt, debris, and liquids by a hermetical seal of the case membrane. The protective casing membrane of the sensor node is designed to prevent ingress of foreign liquid beyond one meter, and achieve an ingress protection rating of up to IP68.

The case membrane, when assembled, creates a void for placement of the electronic circuitry. The void is complete with alignment lips and walls to properly align the electronic circuitry into the void. In this manner, proper alignment between the pin(s), the case membrane, and the electrically conductive fabric is possible. The use of alignment lips, holes, walls, and other features provides a mechanism to properly install and assembly the sensor node(s) with the garment(s). The case membrane provides an electrical connection between the electronic circuitry and the electrically conductive fabric, separating each electrical channel from short circuiting, and incorporating alignment tabs and lips to ensure correct alignment of the electrically conductive fabric, pin(s), and the electronic circuitry. The case membrane provides a structural connection between the garment, conductive fabric, and circuitry. The case membrane also isolates the electrical circuit from the user; it provides protection against electrically shocking the user.

It is preferable that the sensor node case membrane is made from a resilient, tough, and rigid plastic material. It is important to select a material that is compatible with the manufacturing process and one that provides adequate structural rigidity for impact protection, and the ability to create a strong hermetic seal for the circuitry and one or more pin(s) (further discussed below). Some materials may include: Acrylonitrile butadiene styrene (ABS); polycarbonate (PC); ABS and PC mixture; poly(vinyl chloride) (PVC); polyethylenimine (PEI); polyethersulfone (PES); poly(methyl methacrylate) (PMMA); and other suitable materials. Possible manufacturing methods include plastic injection molding, vacuum forming, machining, blow forming, additive printing, and others. The case membrane's finish could be left raw, or it could be painted, clear coated, etc.

Regarding sizing for the case membrane, and specifically volume envelope, typical volumes may range from 352 cubic millimeters and up to 110,000 cubic millimeters, as deemed suitable. Smaller volumes may promote better ergonomics and comfort at the expense of circuitry performance as it relates to wireless signal performance. Typical wall thicknesses may range from 0.89 mm to 5 mm. Thinner walls result in a smaller size, but at the expense of structural rigidity, which may lead in an inability to create a hermetic seal or may provide poor impact protection for the circuitry. Thicker walls could have adverse effects on comfort for the user wearing the garment because the case membrane could be invasive.

Node Pin(s)

The case membrane includes one or more, preferably four, pins, which provide electrical connection between the electronic circuitry and the electrically conductive fabric. These pin(s) also may provide a structural seal against the plastic material. The pin(s), which may be glued, over molded, or compression fitted to the case membrane, is not the same material as the case membrane. These pin(s) can provide a structural seal against the plastic material. The case membrane may provide a structural foundation for one or more pins.

During extreme athletic motion, washing or drying cycles, or other similar load conditions that place significant compression and tension on the electrically conductive fabric, the garment(s), or the case membrane, the pin(s) may be subjected to a radial force which may create a bending force or other similar types of forces. The structural connection between the pin(s) and the case membrane withstand shear or yield in any fashion from more than 20 pounds of external force.

The pin(s) acts as an electrical conduit by creating an electrical connection between the conductive fabric and the circuitry. The pin(s) is designed to penetrate the conductive fabric in areas where there are conductive fiber(s) or materials. This penetrate method creates a void through the fabric, and the conductive fiber(s) or materials "hug" the pin(s), creating a good electrical connection (FIG. 35). In a separate version, the pin(s) "hug" the conductive fiber(s) or materials, creating a good electrical connection. The opposite end of the pin is pressed against the circuitry on specific conductive pads to establish an electrical connection between the pin(s) and the electronic circuitry. The pin(s) transmits, for example, from 300 micro amps to 10 milliamps. The pin(s) facilitates connection to power, ground, and one or more signal channels.

The pin(s) are preferably made from highly electrically conductive materials, such as (for example) brass, copper, or silver. Regarding volume envelope, typical volumes can range from 12.5 cubic millimeters to 400 cubic millimeters. The material of the pin(s) should be selected to provide adequate structural rigidity and to withstand any cantilever forces that are placed on the pin(s) as the electrically conductive fabric migrates during exercise. It is also important to select a geometry that creates a connection with the conductive fabric. Possible manufacturing methods for the pin(s) include lathe, screw machine, investment casting, sand casting, etc. The pin(s) finish could be left raw, or could have conductive paste coatings or other suitable coatings that do not interfere with functionality.

Electronic Circuitry

Figure 9:
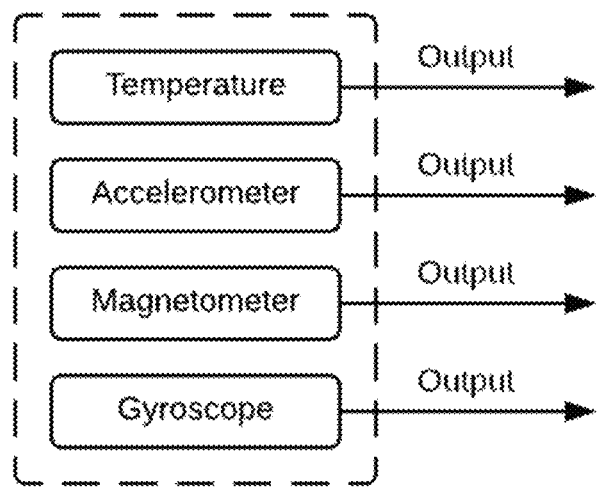
FIGS. 9-18 depict alternative exemplary versions of a sensor node electronic circuitry layout.
Figure 10:
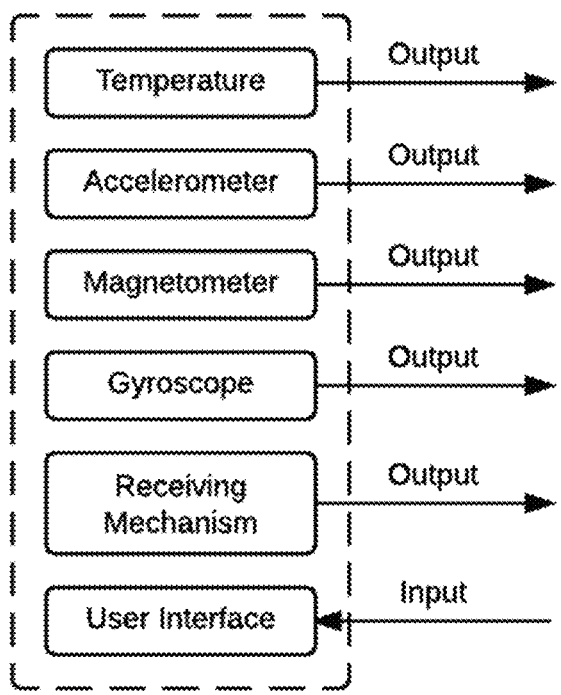
Figure 11:
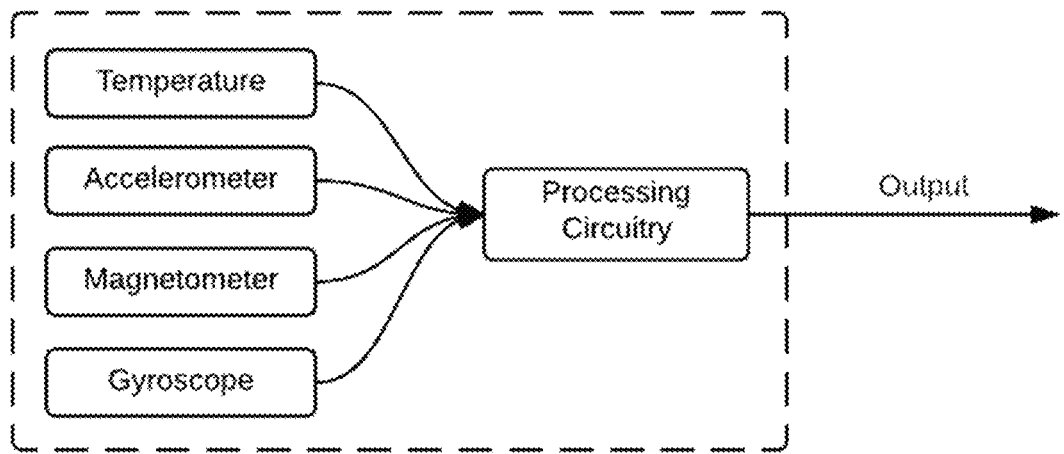
Figure 12:
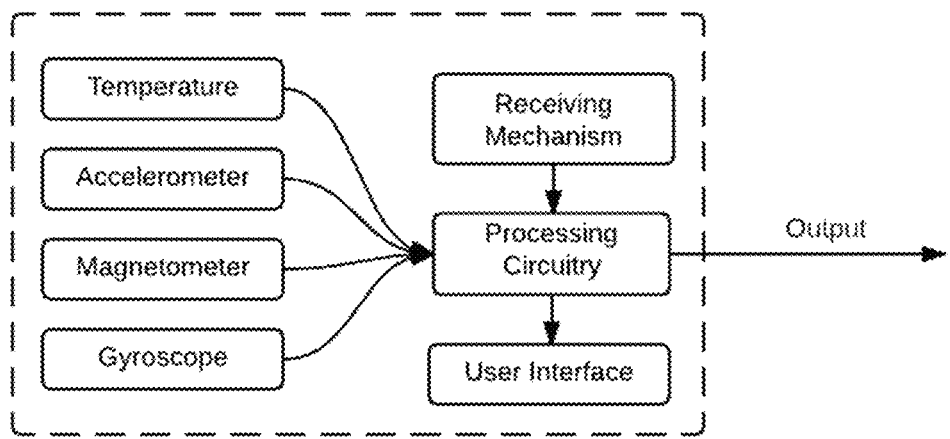
Figure 13:
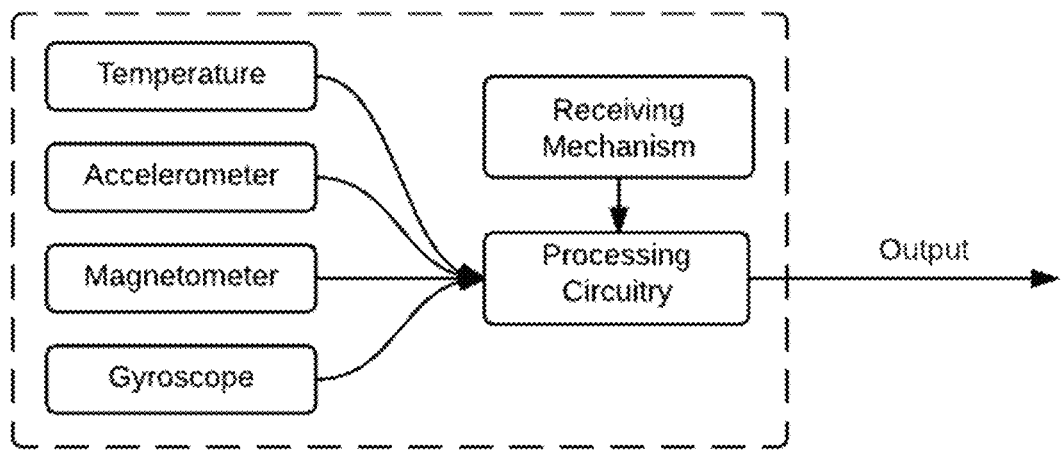
Figure 14:
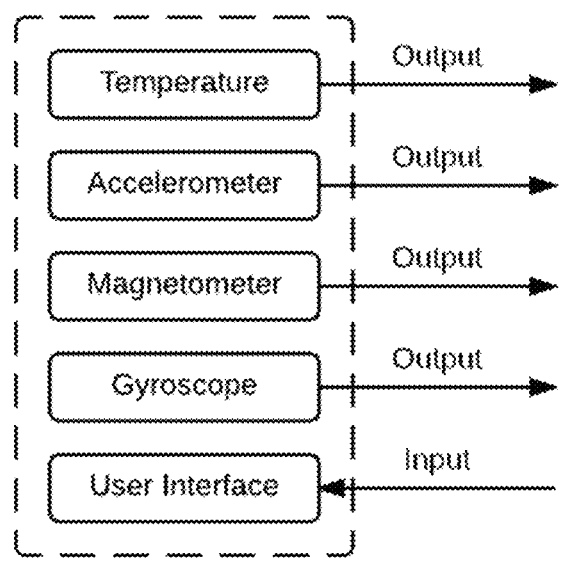
Figure 15:
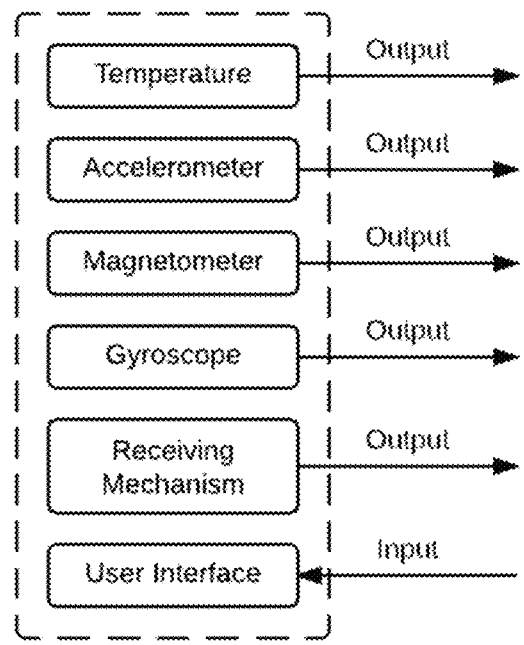
Figure 16:
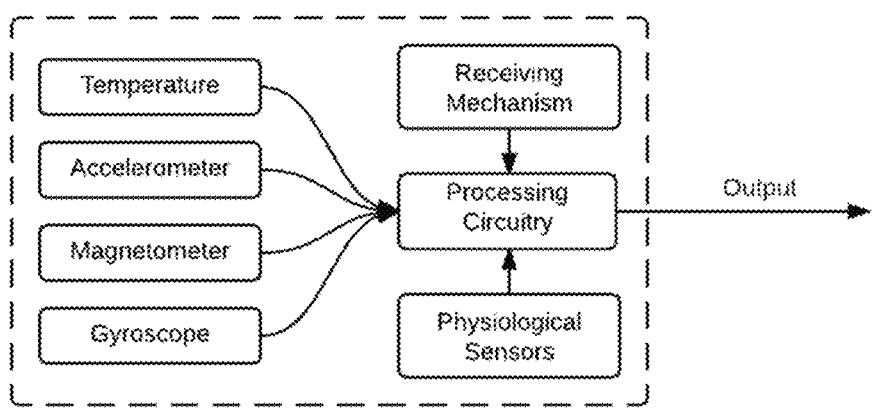
Figure 17:
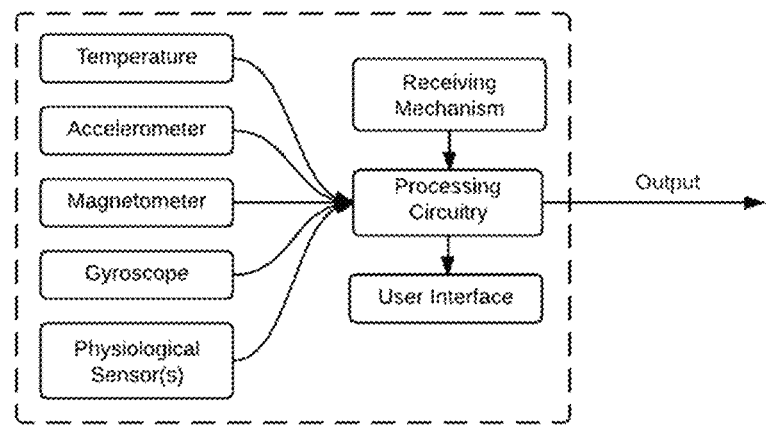
Figure 18:
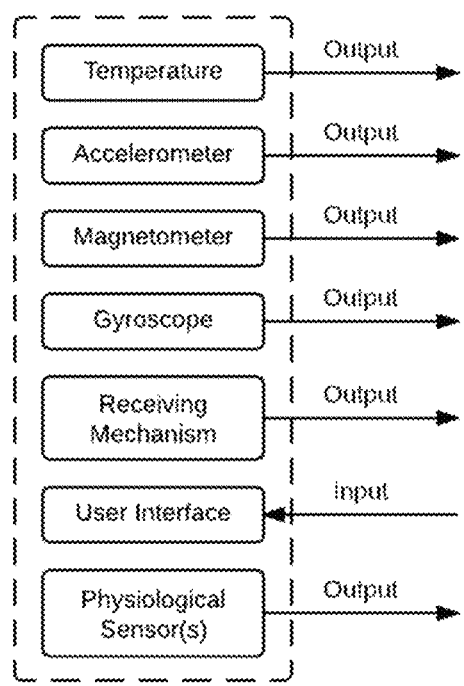

The sensory technology used to gather measurements are typically small electrical components, such as Integrated Circuits (IC), that are typically Surface-Mount Technology (SMT) style components that are attached on a Printed Circuit Board (PCB). Different types of sensors that gather different types of measurements—such as heart rate, blood oxygen, temperature, pressure, altitude, acceleration rotation rate, magnetic flux, etc.—can be fitted within the case membrane of the sensor node. In particular, it is preferable to equip the electronic circuitry with motion sensors—such as 3-axis accelerometers, 3-axis gyroscopes, and 3-axis magnetometers (AMG)—coupled with the necessary IC and System-on-Chip (SoC) to develop a system for analyzing the kinematics of human motion (FIG. 9). In other versions, multiple different measurements, such as heart rate, blood oxygen, skin temperature, etc., could be coupled with a 9-axis AMG system for more data visualization and various specialized applications (FIG. 16).

The motion sensors measure relative movement against an inertial world reference frame. The case membrane provides alignment of the motion sensors to ensure it is possible to align the sensor with the human body to measure accurate kinematics of human motion.

Electrical components can include, but are not limited to, a combination of (FIG. 9 through FIG. 18):

(1) PCB: Used as a mounting platform for all the SMT style components;

(2) SMT style components (FIG. 9 through FIG. 18):
  (i) 3 axis-accelerometer for measuring acceleration;
  (ii) 3 axis-gyroscope for measuring rotation and rotation rate;
  (iii) 3 axis-magnetometer for measuring local magnetic field;

(3) One or more microprocessor(s) (FIGS. 11, 12, 13, 16, 17): Used for computation(s) and for connection and operation of the SMT components;

(4) Physiological sensors (FIGS. 16, 17, 18): these sensors measure an organism's normal functioning, in this case related to vitals such as body temperature, heart rate, blood oxygen, muscle activity, sweat constituents, etc.;
  (i) may include optical heart rate monitor or electrocardiogram, which could be helpful in determining maximum heart rate with respect to athletic movements or exercise;
  (ii) may include muscle impulses (electromyography), which could be helpful in determining muscle activity and the impact of movements on specific muscle groups;
  (iii) may include skin temperature sensor, which could be helpful for knowing the skin temperature to derive core temperature, and for helping improve the accuracy of caloric expenditure and other metrics;

(5) Temperature sensor (FIG. 9 through FIG. 18): there may be a sensor that measures temperature of the circuitry for temperature compensation; this temperature sensor could take measurements of a specific location on the PCB;

(6) User interface components (FIGS. 10, 12, 13, 14, 15, 16, 17, 18):
  (i) Receiving component: Used for turning on power to the circuit or providing general inputs into the system; can be a toggle switch, button, knob, control, etc.;
  (ii) Light-emitting diodes (LEDs): Could be helpful to provide notifications;
  (iii) Vibration motors: Could be used to provide general notifications.

(7) RF components: there may be components that transmit and receive information over wireless channels.

The electrical circuitry may include one or more electrical connection channels, including, but not limited to power, ground, and signal. Preferably, the circuitry is constructed using typical and industry-standard circuitry materials for PCB manufacturing, such as solder, copper, silicone, Mylar, and more. Typical size requirements range from 352 cubic millimeters and up to 110000 cubic millimeters. Smaller volumes promote better ergonomics and comfort at the expense of circuitry performance as it relates to wireless signal performance. The electronic circuit boards could have a PCB manufactured using typical industry standards and processes, and assembly could be accomplished using industry standards and processes for SMT-style components.

Sensor Bands

Some users may not like to wear long sleeve shirts or pants and would rather wear short sleeve shirts and shorts. As such, the sensor nodes(s), sensor module(s), and electrically conductive fabric may not reach the wrists or ankles to measure motion. To address this issue, left and right wrist bands and ankle bands may be used to acquire full body motion data. Some users may not like to wear garments and prefer to interact with a system of one or more sensors bands. Other locations include the wrists, upper arms, torso, hip, thighs, shins, hands (including are all fingers and palms), feet, and head. If desired, a left or right sensor band(s) may be substituted with a smart wrist device or a device equivalent to a smart watch or fitness band, such as a Fitbit HR or Apple Watch, to analyze motion, if the substituting device has an accelerometer, magnetometer, and/or a gyroscope with a compatible wireless internet protocol such that it can synchronize and connect with the system to transmit data and provide feedback. The system may transmit data to and from the third-party device to use any unique sensors it may have to aid in providing data visualization and help in guiding the user on achieving performance goals. The sensor band(s) can communicate to the wireless-enabled computing device through any communications protocol deemed suitable. The sensor bands may also first connect directly to a remote server, then to the mobile or stationary computing device through (for example) the internet. The sensor bands could also connect wirelessly to the sensor module. The electronic circuitry can share the same types of configurations as the sensor module; however, it would not interact with the electrically conductive fabric.

The sensor band(s) preferably have a compact and non-invasive enclosure, attaching securely to the surface of the human body. The enclosure protects the electronic circuitry from impacts and foreign contaminants such as water, debris, dirt, or anything else that could interfere with circuitry operation. The hard or soft enclosure (FIG. 19) produced from modern manufacturing techniques and materials enclose the personal sensing device(s) circuitry to provide modular functionality relating to installation and removal, or can be directly integrated into several user mounting mechanisms including, but not limited to, (for example) shirts, shorts, tee-shirts pants, gloves, hats, helmets, flexible membrane strap, or a combination thereof. The material preferably would not have any adverse effects causing skin irritation, and would provide good ergonomics for maximum comfort. The enclosures of the sensor bands can use the same manufacturing methods identified in the sensor node section. The enclosure of the sensor band could use the same manufacturing methods identified in the sensor node section.

Figure 19:
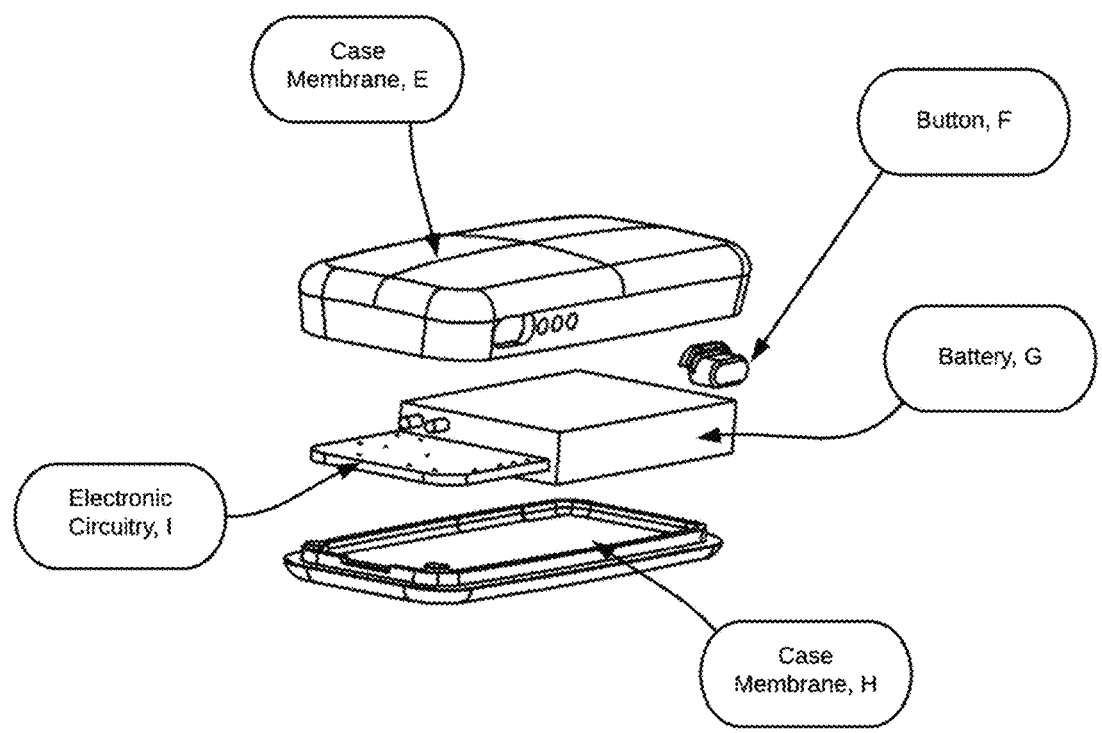
FIG. 19 shows an exemplary layout for a sensor band.
Figure 20:
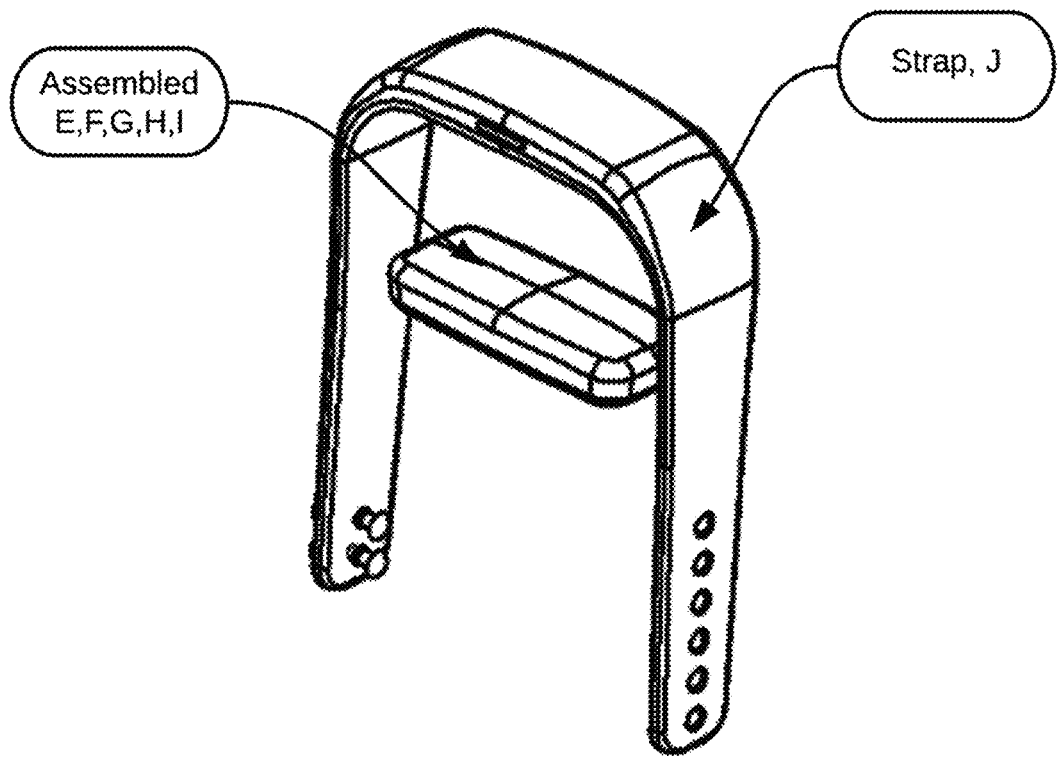
FIG. 20 depicts assembly of an exemplary sensor band.

A flexible membrane strap (FIG. 20) conforms tightly to the exterior geometry of the personal sensing device (FIG. 19). The sensor enclosure can be incorporated into the flexible membrane strap or can incorporate a removable or attachable separate soft or hard enclosure, which can be constrained in a variety of ways including, but not limited to, interference fit, preload by fasteners, or a locking mechanism. The tight conformability allows the user to interface with features, such as buttons, switches, and accessory ports, while protecting from dirt, debris, water, and impulsive force. Alternatively, it may provide openings for features, such as buttons, switches, and accessory ports for ergonomic purposes. The flexible membrane strap provides openings or a thin wall thickness for which light may permeate with adequate visibility for the user to access ports such as a visual display that includes, for example, LED, AMOLED, PMOLED, E-INK, and switches.

Sensor Module

The sensor module, which is configured to allow the garment to withstand multiple machine washing and drying cycles and harsh conditions while exercising, collects accurate sensor measurements from sensor nodes. There are three primary components that make the sensor module: module case membrane, module electronic circuitry, and the module firmware.

Case Membrane

Figure 21:
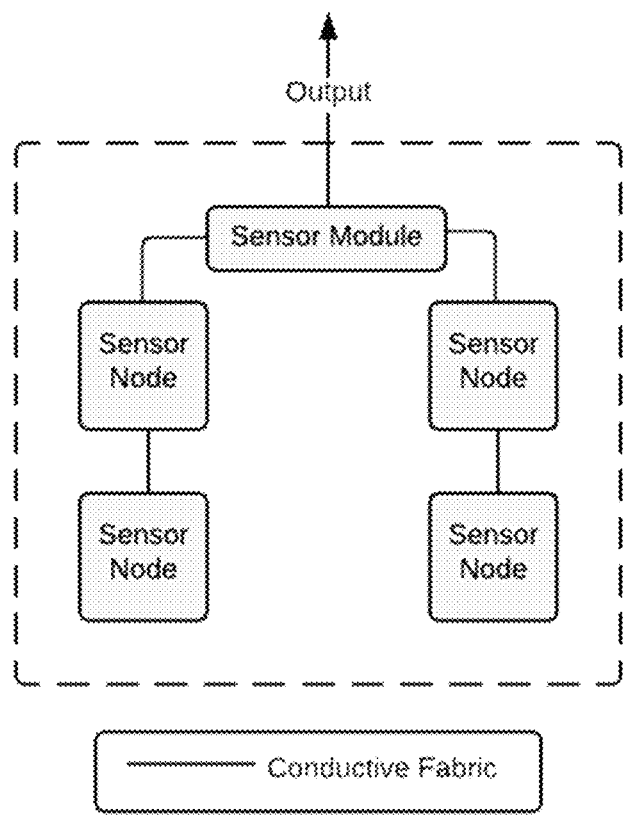
FIG. 21 depicts an exemplary interaction between sensor nodes and sensor modules.

The case membrane houses and protects the electronic circuitry and provides physical alignment features to hold the sensitive electronic circuitry in place (with respect to the human body) to make it possible for the garment(s) to record accurate and precise measurements. It also interacts with the electrically conductive fabric in a very unique and robust manner to enable the system to withstand a plurality of machine washing and drying cycles. As discussed above, the sensor module can be connected with each of two pairs of sensor nodes, each pair of sensor nodes having two sensor nodes connected with each other in series (FIG. 21). A sensor module may be placed on, for example, wrists, upper arms, torso, hip, thigs, shins, or feet. The sensor module(s) are preferably removable and re-attachable. The sensor module(s) can be (for example) clipped, latched, or fastened into a holster that is permanently integrated into the garment(s). Easy removal of the sensor module can make maintenance (repair) and battery charging easier.

Electronic Circuitry

As with the sensor nodes and bands, the electronics use industry standard manufacturing techniques, having a form factor and packaging that is unique and designed specifically to fit within the case membrane. The sensory technology used to gather measurements are typically small electrical components, such as Integrated Circuits (IC), that are typically Surface-Mount Technology (SMT) style components that are attached on a Printed Circuit Board (PCB). The sensor module preferably includes wireless transmission circuitry, such as low-energy Bluetooth to keep energy consumption low and to help maintain small component size. Other protocols, such as UWB, Wireless Fidelity (WiFi), Wi Max, Edge, CDMA, Global System for Mobile Communications (GSM), WCDMA, Metropolitan Area Network (MAN), Wide Area Network (WAN), Personal Communication Services (PCS), General Packet Radio Service (GPRS), Advanced Mobile Phone System (AMPS), 4G, 5G, and other variants of 802.x standards, and varying ranges, throughputs, and frequencies can be used depending on the specific usage application. The sensor module may also connect directly to a remote server through the aforementioned internet networks to send data to be processed, then transmitted to the GUI of a computing device to provide feedback. The sensor module may interact wirelessly with the sensor node(s) and the sensor band(s): the sensor node(s) and sensor band(s) may wirelessly connect to transmit unprocessed data to and from sensor module. The sensor modules can incorporate firmware using coding languages as discussed above with respect to the sensor nodes. The sensor module(s) can connect directly with, and collect unprocessed data from, the sensor node(s) and the sensor band(s), if applicable. Computations can occur on the on-board processing circuitry and include, for example: signal processing, compensations, filtering, and error handling, analogous to the above discussion.

Module Case Membrane

Figure 22:
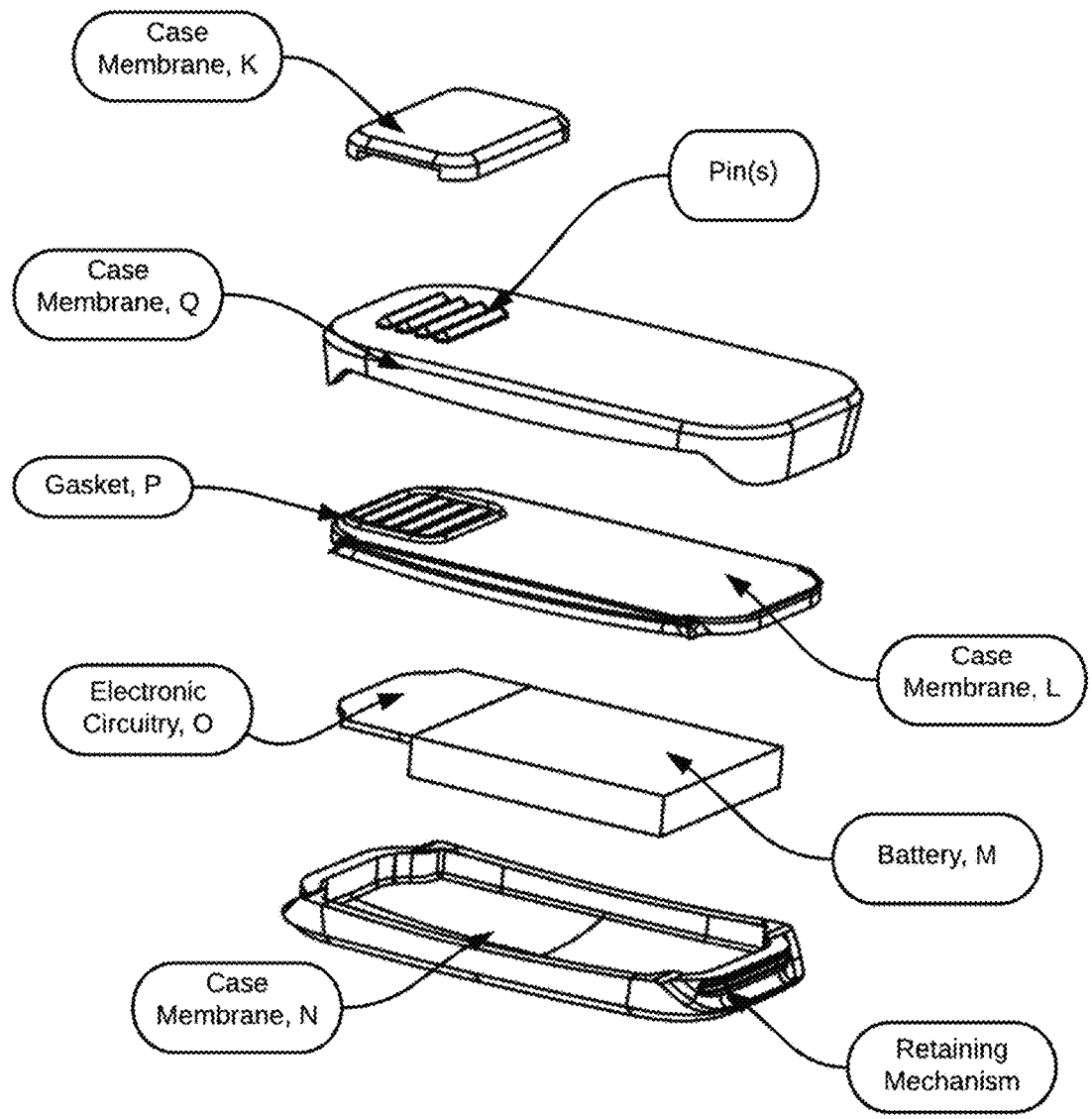
FIG. 22 shows a holster and brain(s) of an exemplary sensor module.

The sensor module can include a four-piece case membrane (FIG. 22):

Part Q: The holster. The holster is permanently attached onto the garment with a retaining mechanism involving a latching, clipping, fastening, or a combination thereof to capture Assembled Parts L, M, N, O, and P in an easy to remove and install manner. The holster interacts directly with the garment and the conductive fabric in the same way as the sensor node. It features one or more pins which directly penetrate and interact with the conductive fabric (FIG. 35). The holster uses those same pin(s) to make contact with the Assembled Parts L, N, and O.

Assembled Parts L and N: These parts house all electronic circuitry and provide pin(s) which interact with the pin(s) that are bonded within the holster. These parts can have feature(s) which can interact with Part Q to accommodate a retaining mechanism involving latching, clipping, fastening, or a combination thereof.

Part K: The Cover. The cover is permanently attached onto the garment in the final stages of assembly. Its primary purpose is to secure Part Q onto the garment and to provide alignment and protection for the electrically conductive fabric, the pin(s), and the garment. The sensor module may incorporate one or more of Part K to help stabilize and provide greater contact area between the garment and Part Q for a more durable connection. It provides protection to the circuitry against impact forces, such as drops of more than 90 g. It provides protection for the circuitry and all other supporting electrical components against dirt, debris, and liquids by a hermetical seal of the case membrane. The protective casing membrane of the sensor module is intended to prevent ingress of foreign liquid beyond one meter and achieve an ingress protection rating of up to IP68.

Parts N and L: The assembled case membrane includes a void for the electronic circuitry. The void can include alignment lips and walls to properly align the electronic circuitry into the void. In this manner, proper alignment between the pin(s), the case membrane, and the conductive fabric is ensured.

The module case membrane provides electrical connection between the circuitry and the electrically conductive fabric. It separates each electrical channel from short circuiting with another, and it provides a structural connection between the garment(s), electrically conductive fabric, and electronic circuitry. The module case membrane isolates the electrical circuit from the user; it provides protection against electrical shocks to the user.

Module Pin(s)

The pin(s), which may be glued, over molded, or compression fitted to the case membrane, is not the same material as the case membrane. These pin(s) can provide a structural seal against the plastic material. The case membrane may provide a structural foundation for one or more pins. During extreme athletic motion, washing or drying cycles, or other similar load conditions where there is compression and tension placed on the electrically conductive fabric, the garment(s), or the case membrane, the pin(s) may be subjected to a radial force which may create a bending force or other similar types of forces. The structural connection between the pin(s) and the case membrane should not shear or yield in any fashion from (for example) 20 or more pounds of external force.

The pin(s) acts as an electrical conduit by creating an electrical connection between the conductive fabric and the circuitry. The pin(s) penetrates the conductive fabric in areas where there are conductive fiber(s) or materials (FIG. 35). This penetration method creates a void through the fabric and the conductive fiber(s) or materials "hug" the pin(s), creating a good electrical connection. In alternative versions, the pin(s) "hug" the electrically conductive fiber(s) or materials. The opposite end of the pin(s) is pressed against the circuitry on specific solder pads to establish an electrical connection between the pin(s) and the electronic circuitry. The pin(s) is designed to transmit from 300 microamps to 10 milliamps. The pin(s) facilitates connection to power, ground, and one or more signal channels Gasket Because the pin(s) can be used to provide an electrical connection between the holster and the sensor module, the pin(s) may be exposed to contaminants when the user is wearing the garment(s) and performing exercises or otherwise making athletic movements. Since the system may be subjected to a variety of harsh environments, such as extreme heat, swimming pools (and the chemicals therein), extreme cold, etc., it is beneficial to protect the pin(s) against foreign contaminants, such as liquid, dirt, debris, sweat, etc. A gasket or other type of compression device that forms a closed ring about the pin(s) is used to provide protection and create a hermetic seal for the pin(s). The gasket seal can be effective when the sensor module is installed on the holster, and is properly attached and aligned in such a way that the compression device creates high localized stresses, which do not yield the material, but provide adequate sealing pressure. The gasket is made from a pliable material to be compressed between the holster and the sensor module.

Materials

Case Membrane—Part L, N, Q, and K: It is preferable that the sensor module case membrane is made from a resilient, tough, and rigid plastic material. It is important to select a material that is compatible with the manufacturing process and one that provides adequate structural rigidity for impact protection, shear, torsional loads, etc., while providing the ability to create a strong hermetic seal for the electronic circuitry and one or more pin(s). Some materials include: ABS, polycarbonate, an ABS and PC mixture, PVC, PEI, PES, PMMA, and materials deemed suitable.

The case membrane includes one or more pins, preferably eight pins, which provide electrical connection between the electronic circuitry and the electrically conductive fabric. Preferably, the pin(s) are made from highly electrically conductive materials, such as brass, copper, or silver.

The gasket preferably is made using materials with pliable characteristics, and that are resilient to detergents and solvents, such as laundry detergent, water, oil, and debris. The durometer of such gaskets can range from 10 A to 70 A Shore. Suitable materials may be silicone, polytetrafluoroethylene (PTFE), neoprene, Buna-N (nitrile rubber), etc.

Size

Volume envelope for the module case membrane (parts L, N, Q, and K) can range from 352 cubic millimeters up to 110000 cubic millimeters. Smaller volumes promote better ergonomics and comfort at the expense of circuitry performance as it relates to wireless signal performance. Typical wall thicknesses may range from 0.89 mm to 5 mm. Thinner walls result in a smaller size, but at the expense of structural rigidity, which may lead in an inability to create a hermetic seal or poor impact protection for the circuitry.

Volume envelope for the pin(s) can range from 12.5 cubic millimeters up to 400 cubic millimeters. The pin(s) should have a geometry that provides enough structural rigidity to withstand cantilever forces that are placed on the pin(s) as the conductive fabric may migrate during exercise. It is also important to select a geometry that creates a connection with the conductive fabric.

Manufacturing Methods and Finishes

Possible methods for manufacturing the module case membrane and gasket (Parts L, N, Q, K, and P) are plastic injection molding, vacuum forming, machining, blow forming, etc. Potential methods for manufacturing the pin(s) include lathe, screw machine, investment casting, sand casting, and more. The module case membrane can be finished as the sensor case membranes.

Electronic Circuitry

As with the sensor nodes, the electrical components can include, for example, a PCB used as a mounting platform for all the SMT style components (such as accelerometers, gyroscopes, and magnetometers. The sensor module can include user interface with a receiving component for inputs into the system, and LEDs and vibration motors for visual and tactile cues, instructions, notifications, and warnings. The wireless transmission circuitry can include the various wireless protocols requiring an antenna, but the antenna geometry will vary for different protocols, such as UWB, Bluetooth, Wireless Fidelity (WiFi), Wi Max, Edge, CDMA, Global System for Mobile Communications (GSM), WCDMA, Metropolitan Area Network (MAN), Wide Area Network (WAN), Personal Communication Services (PCS), General Packet Radio Service (GPRS), Advanced Mobile Phone System (AMPS), 4G, 5G, and variants of 802.x standards, and varying ranges, throughputs, and frequencies. Near field communication technology may be incorporated as well.

A system on chip (SoC), which is a packaged integrated circuit (IC) that integrates all components of an electronic system, such as (for example) Bluetooth, WiFi, processing, etc., can be used. Typically, the wireless transmission circuitry is packaged within a SoC. One or more radios for receiving and or transmitting of data for one or more wireless transmission links can be included (FIGS. 24 to 30). The radios may serve as remote station for other devices, such as the sensor node(s) and sensor band(s) connecting wirelessly with the sensor module, which could then communicate with the wireless-enabled computing device. Direct connections using conductive materials, such as (for example) electrically conductive fabric or wires, would not be necessary.

The sensor module includes a battery (FIGS. 24 to 30), such as a lithium polymer-ion or any other modern chemistry suitable for consumer grade products. The lithium polymer battery is not removable, so as to maintain seals and otherwise avoid compromising integrity; if the battery is removed, the entire sensor module unit would likely need to be replaced. Inductive coupling components could be beneficial to provide wireless charging as well as contactless connections between the holster and the brain case membrane. This way, there would be a lower likelihood of the module case membrane breaking, and fewer opportunities for a leak path to originate because there are fewer apertures present.

Microprocessor(s) for computations and for connecting and operating SMT components, a SoC with wireless transmission circuitry packaged therein, and physiological sensors could be used as with the sensor nodes (FIGS. 24 to 30). Random Access Memory (RAM) would be used to store processed or unprocessed data from sensor node(s) and band(s) for times when the sensor module is not able to exchange data with the wireless-enabled computing device (and/or the server) (FIGS. 27 to 30). For example, if a user is swimming while wearing a smart garment, and water is absorbing/dampening signals (and preventing transmission of wireless data), the RAM could be used to temporarily store data until the data can be transmitted.

The electrical circuitry may have one or more electrical connection channels, including, but not limited to, power, ground, and signal. The sensor module may communicate with the sensor nodes through protocols including, but not limited to, Inter IC bus (I2C), synchronous serial interface (SSI), serial peripheral interface (SPI), universal asynchronous receiver/transmitter (UART), pulse-width modulation (PWM), pulse-code modulation (PCM), and other types of serial communications protocols.

Typical size requirements can range from 22,600 cubic millimeters up to 90,500 cubic millimeters. Smaller volumes promote better ergonomics and comfort at the expense of circuitry performance as it relates to wireless signal performance. The circuitry may be constructed using standard materials for PCB manufacturing, such as solder, copper, silicone, etc. A PCB may be manufactured first, before SMT-style components are assembled using relevant industry standards and processes.

Electrically Conductive Fabric

The primary role of the conductive fabric is to transmit data and power throughout a garment in a comfortable, aesthetically appealing, safe, and cost effective manner. Several devices can be connected together to transmit power and ground signals and one or more data transmissions, in a manner that has low electronic signal attenuation. If there is high signal attenuation, it will affect the data rate transmission between the sensor nodes and the sensor module. The goal is to have fast data rates to minimize on measurement latency. Ideal electrical characteristics could resemble those of a typical 28-30 gauge copper wire.

The electrically conductive fabric is designed to be stretchable, thin and light weight; the electronically conductive fabric is integrated directly into the garments without intruding on the function of the garment as sports outerwear. The electrically conductive fabric is designed to provide a water proof connection between the sensor node(s) and sensor module(s). The electrically conductive fabric is fully submerged in a textile coating to isolate the user from electrical shock, which would cause discomfort to the user, although the power levels are generally not high enough to be life threatening unless the user has a pacemaker.

The conductive fabric can reduce costs by lowering total part count. Because the conductive fabric connects all the sensor nodes together to the sensor module, the need for multiple batteries, Bluetooth antennas, microprocessors, and more are eliminated because many of these parts are consolidated and placed within the sensor module(s).

Configurations

The conductive fabric can range in thickness from 0.45 mm up to 4 mm. The fabric's width can range from 6 mm to 15 mm, and total length for each fabric (combined shirt and pants) may range from 1 m upwards, depending on the user's body lengths. For instance, garment(s) for children could be as low as 1 m.

The conductive fabric includes one or more separate conductive yarn or wire channels. It is important to isolate the separate conductive yarn or wire channels from one another to avoid short circuiting. It is also important to create a pattern that maintains a constant distance between adjacent conductive yarn channels. The composition and mixture of the conductive yarn or wire as it relates to electrical characteristics is important. Exemplary configurations characteristics follow.

Linear Distance: The distance between each conductive yarn channel can range from 1 mm to 4 mm (center to center), preferably 2.3 mm (see FIG. 31). This regulates the distance of the pin(s) for the sensor node(s) and sensor module(s). It is important to maintain this linear distance or the pin(s) may not be able to make a good electrical connection, which would render the garment(s) defective or otherwise nonfunctional.

Resistance: The conductive yarn channel preferably does not exceed 50 ohms per 1 m. Maintaining acceptable electrical characteristics can directly affect signal attenuation and data transmission rates. Too high of a resistance will result in poor signal attenuation and low data transmission rates. To achieve the required electrical characteristic specifications, resistivity can be decreased by applying a pitch (twists per length) to bring the individual yarn strands closer together. Whether the conductive material is a fiber, metal, or yarn, this tactic is valid for all conductive materials. In this manner, the conductive surfaces are moved closer together and more within a smaller length. However, the mechanical characteristics of a fiber compared with a metal are significantly different that one material may cold work and break during this type of packing, which presents a limitation to which types of materials this tactic may be applied to. A preferable pitch is 50 to 500 revolutions per meter.

Coating: The coating thickness can range from 0.25 mm to 2 mm. It is important to select a thickness that enables the coating to remain fairly intact during high flexion or stretch conditions. The thinner the material, the more likely that the coating will fall off. However, the thicker the coating, the more likely the user will experience discomfort.

Elongation: It is preferable to have a conductive fabric that has elongation characteristics (along the warp) to be 100% to 120% with a 0.5 kg weight. It is not necessary for the conductive fabric to have elongation characteristics greater than 20% elongation in the weft direction, but it is acceptable. A material with high elongation characteristics will provide a more comfortable experience. Users generally do not prefer materials that constrain movement or provide resistance, although this depends on the application. For example, if the user is training, they may prefer less elongation, as it adds more resistance. However, for performance or competition events, less resistance may be more beneficial to the user's performance.

Electroluminescent yarn: This yarn can be weaved or knitted in the warp or weft. This material would require more power consumption and other electrical circuitry such as an AC inverter. This could be beneficial to include in the garment for general notification purposes.

Figure 23:
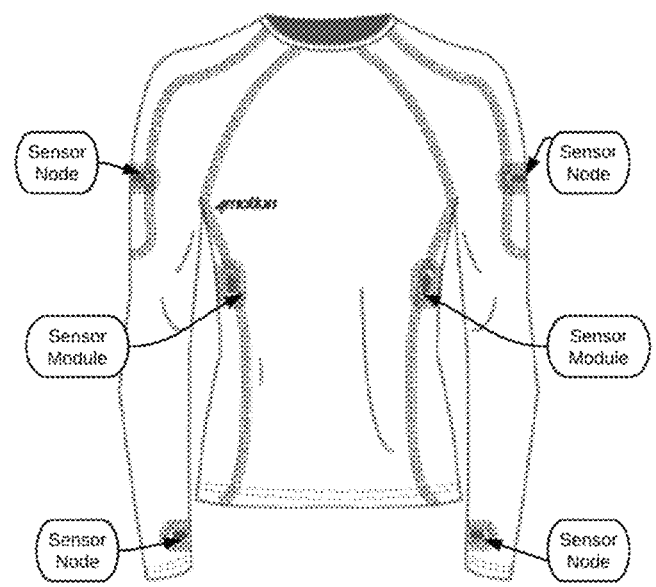
FIG. 23 depicts exemplary garment exemplary positions for sensor nodes and sensor module.
Figure 23:
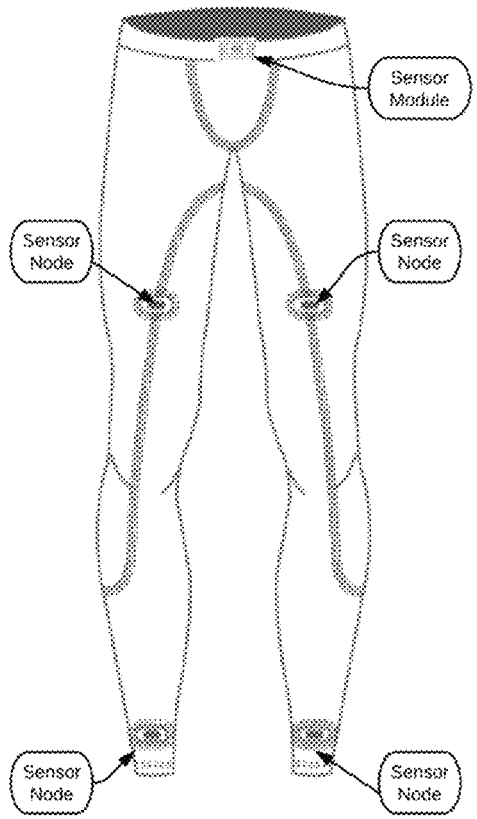
Figure 24:
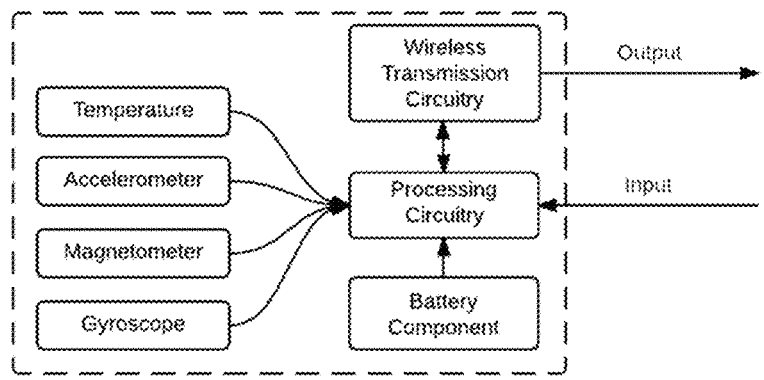
FIGS. 24-30 depict alternative exemplary versions of a sensor module and sensor band electronic circuitry layout.
Figure 25:
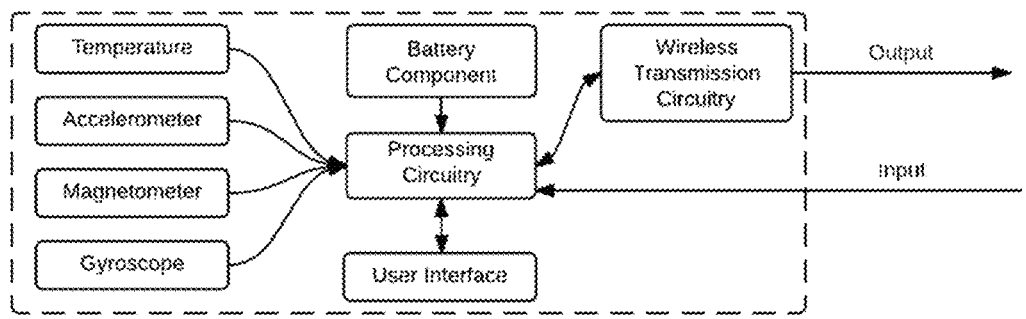
Figure 26:
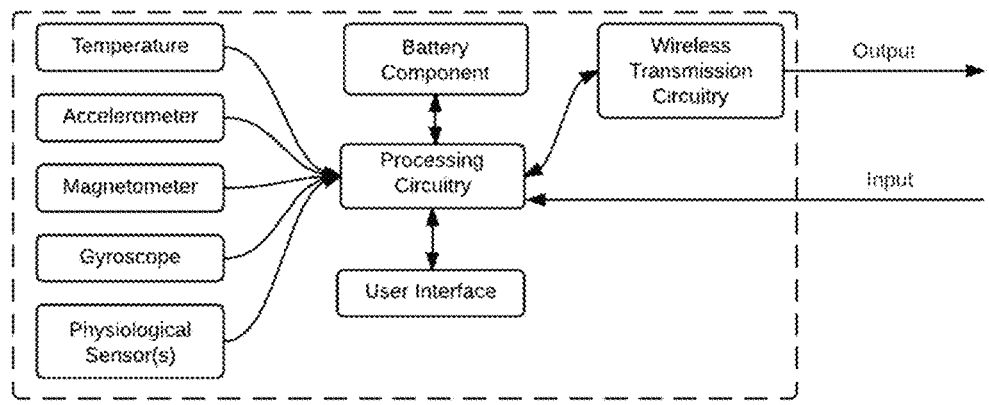
Figure 27:
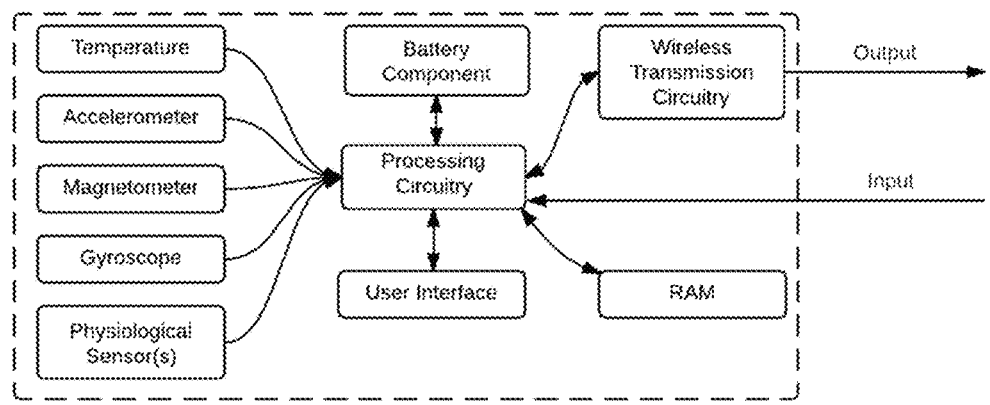
Figure 28:
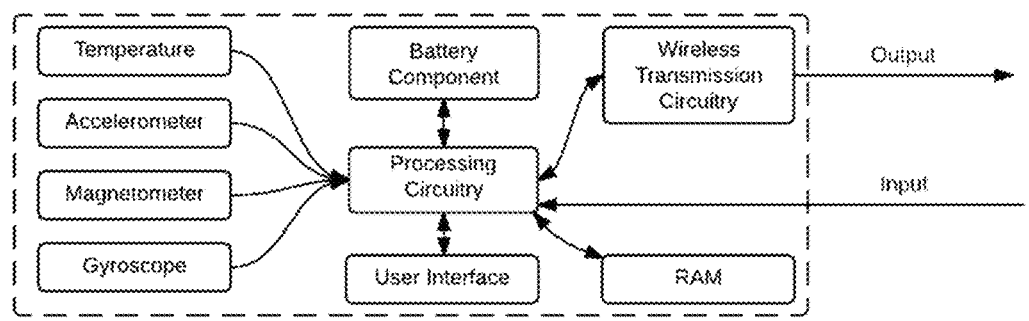
Figure 29:
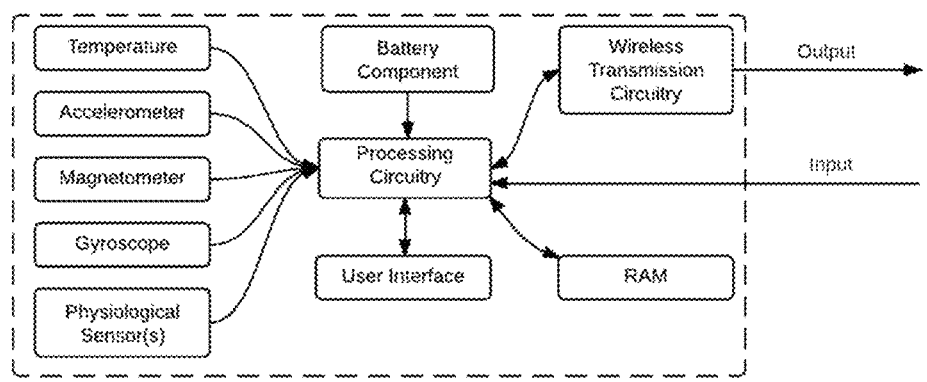
Figure 30:
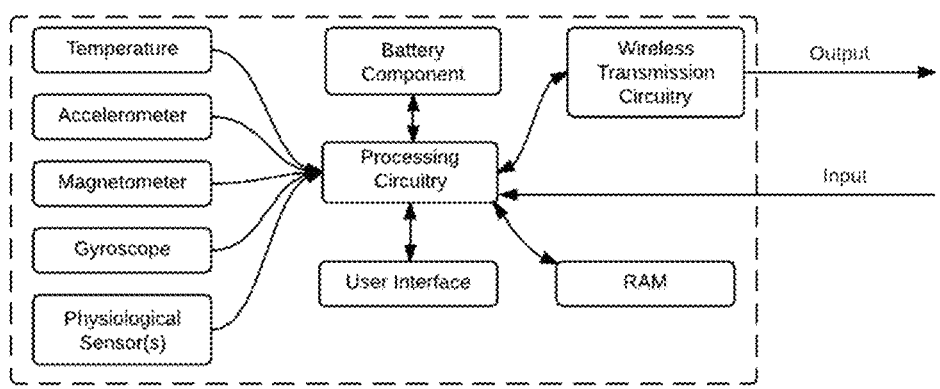

Placement: The electrically conductive fabric can be situated along the length of the arms and legs. The electrically conductive fabric would be situated along the length of the limbs because typically the sensor node(s) are not directly connected, in series, on the electrically conductive fabric. The locations of the sensor node(s) drive the positioning of the electrically conductive fabric (FIG. 23).

Materials

Various electrically conductive materials can be used, depending on application and desired properties:

(1) Metal wire: Typical wire in the range of 20 gauge to 30 gauge, weaved or knitted in the warp of the electrically conductive yarn, can be used. Typical metal wire, such as copper, brass, etc., has very high conductivity and low capacitance, which has excellent signal transmission performance. Furthermore, wire with insulation can also be used as well. However, the material is very fragile and can cold work under repeated flexion and bending.

(2) Conductive metalized yarn: It is important to select electrically conductive yarns that provide adequate electrical and mechanical attributes. However, the electrical characteristics are generally inferior to those of typical metal wires. It is important to achieve electrical characteristics that avoid significant signal attenuation between the sensor module(s) and the sensor node(s). Moreover, it is important to provide a durable fabric structure. It is also important to design a structure that is comfortable and can be easily integrated into the garment. There are various configurations of conductive yarn available for use, such as polyamide 6.6 filament yarn, 99% silver yarn made by Shieldex, denier 520/68f or other various deniers and numbers of ply. Electrically conductive yarns are typically nylon (or other suitable materials) yarn of varying denier and ply, which are plated with conductive non-ferrous metals like copper or silver, or ferrous metals like as stainless steel. Yarns mixed with strands of metal wires or wire meshes with non-conductive yarn may provide more desirable electrical performance.

Base yarn: Highly stretchable, resilient, and cost effective materials, such as polyester or nylon, are preferable. The base yarn is used in the warp and weft. This is a significant component to the electrically conductive fabric as it is used to position and regulate position and performance of the length, width, elongation, etc. The denier of the base yarn can preferably be as small as possible without adversely affecting mechanical and electrical performance. Typically, small denier will be more comfortable to the user because it will result in a thinner part and be less intrusive to the user. The pick (or thread density) should be sufficiently high such that mechanical performance is not sacrificed. A smaller pick will allow the fabric to have more elongation; however, the ability to maintain linear distance of conductive materials is weakened.

Elastomer: The elastomer regulates stretch of the material and acts as a component to bring elasticity into the fabric. Preferable materials include neoprene, butadyl, latex, nitrile or other suitable elastic materials. The elastomer regulates elongation properties and enables the assembled electrically conductive fabric to return to static length. The elastomer should run along the entire length (parallel to the warp) of the electrically conductive fabric, as it is an integral component of the fabric. There may be one or more weft elastomers that run along the length of the electrically conductive fabric. The diameter of the elastomer ranges from 0.25 mm to 1 mm.

Manufacturing: Possible manufacturing methods include knitting or weaving. The pattern for the knit should allow for thin, yet highly stretchable designs. The electrically conductive fabric is created on a specialized narrow fabric weaving machine or a specialized knitting machine.

Finish/Appearance: The electrically conductive fabric will be coated with a textile coating, which may come in a variety of colors, including, but not limited to black, white, and many other options. The textile coating should not be conductive and should possess isolative characteristics to provide protection to the user against electrical shock. It should be able to withstand a plurality of wash and dry cycles as well as various athletic movements and flexion of the sensor node(s), electrically conductive fabric, and sensor module(s).

Installation method: The coating can be deposited based on typical industry standards for textile coatings. Various methods may include, for example, lamination, direct application of a polymer onto the textile surface, or indirect application of a polymer to the textile surface. The insulation methods can use typical industry standard practices and machinery to apply the textile coating.

Coating durability: It is preferable to utilize a coating that is designed for textile applications, such that the coating remains bonded to the fabric under harsh conditions, such as during multiple machine washing and drying cycles, flexion, and torsion.

Durometer: The softness (durometer) is preferably less than 40 Shore A. Softer is preferable for providing more compliance and a stronger seal against contaminants when it is assembled between the casing membrane and the pin(s) of the sensor node(s) and module(s).

Tackiness: The coating should be sufficiently tacky to help maintain and limit relative movement between the garment, sensors, and the user's skin. This is important for sensor accuracy, as high migration of the sensor relative to the calibration can have adverse effects on the output of the feedback and measurement.

Insolation: The coating should fully cover and insulate the conductive fabric to protect the conductive yarn against foreign contaminants such as (for example) dirt, debris, sweat, liquid, or any material that could cause short circuiting or harm/discomfort to the user, and to hold the warp and weft of the yarns in place with respect to all components during flexion, torsion, or elongation. The coating helps regulate the position and can help prevent the conductive yarns from short circuiting upon flexion, torsion, or elongation conditions. Adequate thickness is important to provide redundant sealing mechanisms between the pin(s), sensor node case membrane, and circuitry. Furthermore, the same sealing redundancy can be replicated for the pin(s), sensor module case membrane, and circuitry.

Skin compliance: It is important that the textile coating meet and exceed the standards and requirements of ISO 10993 for skin contact healthcare applications relating to cytotoxicity, skin irritation, and sensitization (allergic) potential.

Materials: mixtures of silicone, rubber, polymers, thermoplastics, and other materials, which meet and exceed standards and requirements of ISO 10993, are suited to adequately coat the conductive fabric.

Figure 31:
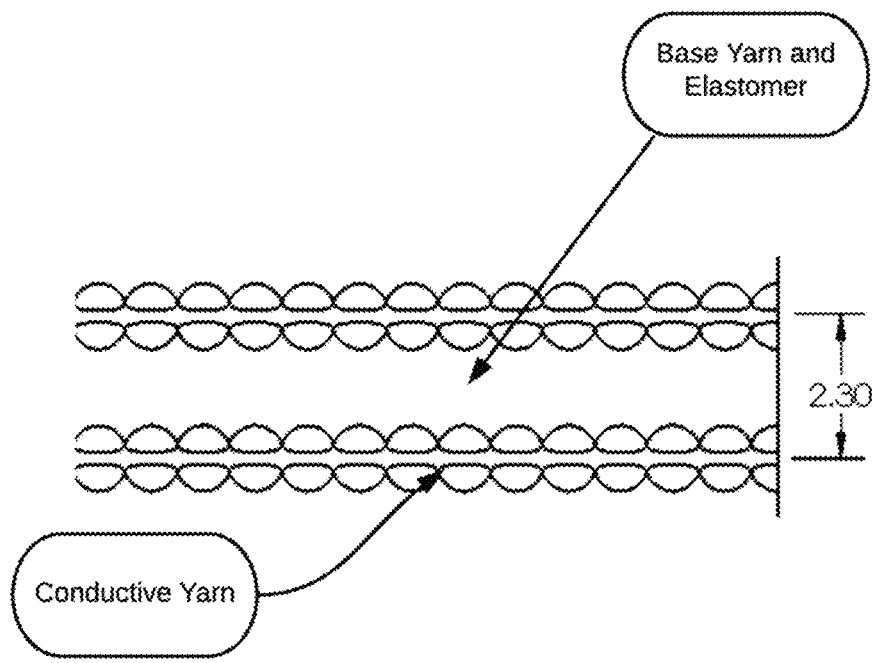
FIG. 31 represents a top view of electrically conductive fabric, in which the four horizontal details are the conductive fabric. The distance of 2.3 mm is the distance between each yarn.

FIG. 31 is a top view of electrically conductive fabric. The 4 horizontal details are the conductive fabric. The distance of 2.3 mm is the distance between each yarn.

Assembly

Figure 32:
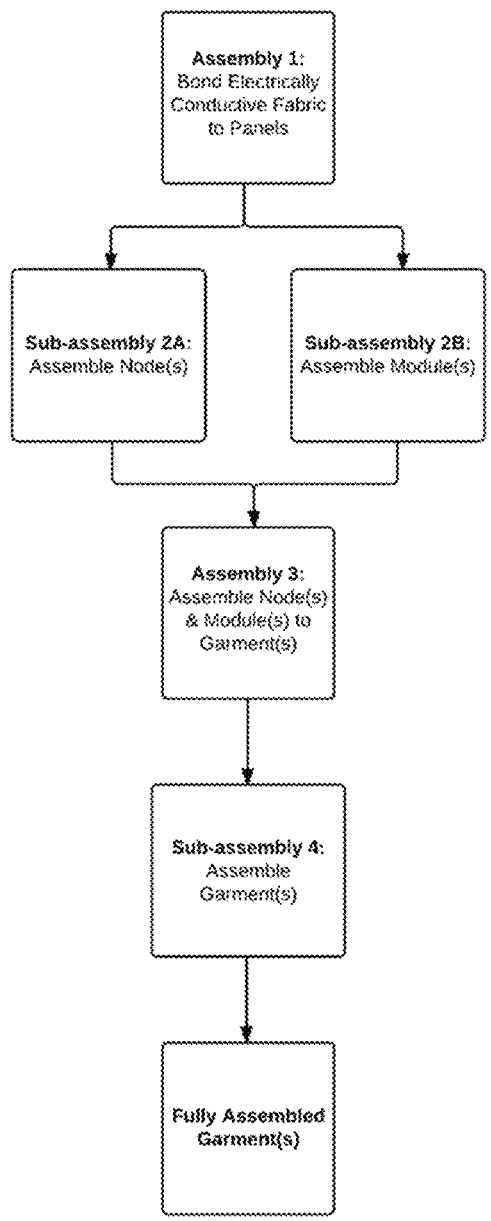
FIGS. 32 and 33 show alternative exemplary assembly processes.
Figure 33:
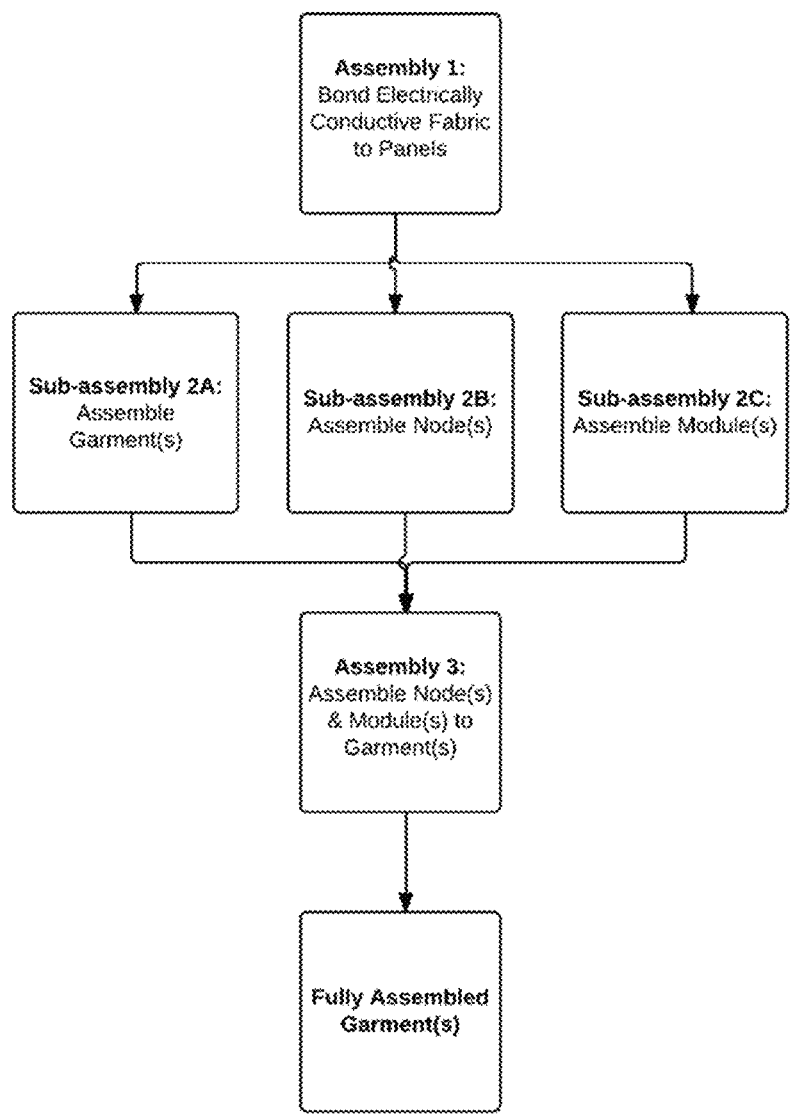

The following assembly process is not intended to limit the possibilities, but rather to provide one or more options for assembly. There are variations of the overall assembly process and combinations thereof. See, e.g., FIGS. 32, 33.

Bond Electrically Conductive Fabric to Panel(s)

(1) Cut and Sew. After the fabric and trim is sourced and the fabric pattern template is created and approved for production, the manufacturing process can begin. The pattern is an outline of each component, such as the sleeve, the back, the chest, etc. These components are often referred to as "panels" in the cut and sew industry. Panels are cut from large sheets of fabric and placed in a fabric cutting machine. The general outline of the panels is cut according to a template; in the fabric industry, this is often referred to as a "pattern." The pattern for the exemplary garments discussed above is unique at least because of its size and the fit of the assembled product.

The machines used during the process depend primarily on the garment unit volume required for delivery. At low production volume, workers typically cut garment panels using scissors from large sheets of fabric. At high production volume, the panel extraction process can be controlled by an automated laser cutting machine that cuts panels from large sheets of fabric.

(2) Bonding Electrically Conductive Fabric. The electrically conductive fabric can be attached to garment by an overlay, sewing, or welding process. The electrically conductive fabric can be placed on the interior or the exterior of the garment, but it does not have an impact on the performance. The decision to place the electrically conductive fabric on the interior or exterior would be based in part on aesthetics and may depend on the applications. If placed on the exterior, it may be beneficial for sensor alignment purposes and awareness for the user. For a discrete appearance, it may be beneficial to install the sensor node(s) and module(s) with the bulk of the case membrane hidden on the interior side of the garment(s).

(i) Overlaying. The conductive fabric can be glued, printed, or screen printed onto the surface of the panel. Electrically conductive fabric can be attached on one or more panels at the same time. This is a preferable interface because it would be most ergonomic and potentially the least labor intensive process (for example: cheaper to manufacture). However, it could take more time associated with dry time of the adhesive. The compound used to adhere the electrically conductive fabric should be stretchable and is preferably skin compliant per ISO 10993 standards.

The machines used in this process include fixtures used to control placement of the electrically conductive fabric onto the panel(s). Fixtures are used to place the electrically conductive fabric on the arms, legs, and torso. Machines used to control the amount of adhesive would be useful so as to not waste adhesive.

(ii) Sewing. The electrically conductive fabric can be sewn onto the seam of the garment, adjoining two cuts together to make a seam. The electrically conductive fabric can be overlaid onto of the seam or juxtaposed to the seam. This would be less optimal than overlaying the conductive fabric through adhesion because the conductive fabric would likely be larger in width to accommodate the placement of the thread that attaches the electrically conductive fabric. This is true because the thread could penetrate and create a leak path to the electrically conductive yarn, which would compromise functionality and durability.

Machines used in this process include fixtures for controlling placement of the electrically conductive fabric onto the panel. Fixtures can be used to place the electrically conductive fabric on the arms, legs, and torso. Typical production sewing machines can be used for the assembly process.

(iii) Welding. The electronically conductive fabric may be ultrasonically welded onto the interior or exterior of the panel. This could prove advantageous because the installation and setup time is quicker and less labor intensive than overlaying and sewing. It may not appear to be most attractive aesthetically because when the panel is welded to the electrically conductive fabric, the surface of the weld may not be homogenous and can have a rough surface finish.

Machines used in this process include fixtures for controlling placement of the electrically conductive fabric onto the panel. Fixtures can be used to place the electrically conductive fabric on the arms, legs, and torso. Typical sonic welding machines with specific fixtures can be used for the assembly process.

Figure 34:
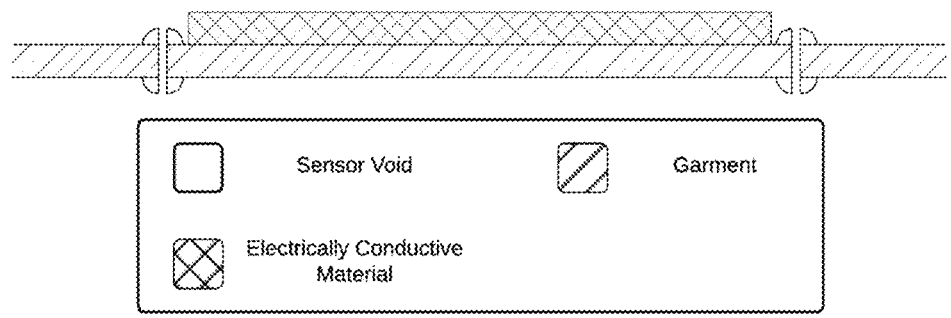
FIG. 34 represents an exemplary sensor void.

(3) Sew sensor voids. Once the electrically conductive fabric is installed onto the garment panels, the sensor voids are created and sewn juxtaposed to the electrically conductive fabric. The placement of these sensor voids corresponds with the location of the sensor node and the sensor module. The placement of these sensor voids can be critical to the accuracy of the measurements taken by the sensor node and module. FIG. 34 shows a sensor void example Assemble Garment(s)

The panels can be sewn together using typical production style sewing machines, with a worker sewing the panels together. The worker can align each panel together and stitch accordingly. This can involve sewing machines and some fixtures for aligning panels together.

Assemble Node(s)

Step 1: Gather parts (parts A, B, C, and D).

Step 2: Set part C into alignment fixture with void facing up. The alignment fixture guides the assembly worker to orient the part in the most ergonomic way.

Step 3: Align and place part D into void, making sure conductive pads are visible.

Step 4: Align part B on top of parts D and C. The alignment features built into part B will provide smooth engagement.

Step 5: Bond parts B and C together. Machines that can be used in this process include a sonic welder, press, or clamping mechanisms.

Assemble Band(s)

Step 1: Gather parts (parts E, F, G, I, and H)

Step 2: Set part E into alignment fixture with void facing up. The alignment fixture can guide the assembly worker to orient the part ergonomically way.

Step 3: Align and place parts F, G, and I into void.

Step 4: Align part H on top of parts E, F, G, and I. The alignment features built into part H will provide smooth engagement.

Step 5: Bond parts H and E together. Machines that can be used in this process include a sonic welder, press, or clamping mechanisms.

Step 6: Insert assembled parts E, F, G, H, and I into part J.

Assemble Module(s)

Step 1: Gather parts (parts K, L, M, N, O, P, Q)

Step 2: Set Part N into alignment fixture with void facing up. The alignment fixture guides the assembly worker to orient the part in an ergonomic manner.

Step 3: Align and place parts M and O into void.

Step 4: Align part L on top of parts N, M, and O. The alignment features built into part L will provide smooth engagement Step 5: Bond parts L and M together.

Machines that can be used in this process include a sonic welder, press, or clamping mechanisms.

Assemble Node(s) and Module(s) to Garment(s)

(1) Assemble Sensor Nodes and Sensor Modules to Shirt and Pants

The sensor node is installed on the interior or the exterior of the garment. If placed on the exterior, it may be beneficial for sensor alignment purposes and awareness for the user. For a discrete appearance, it may be beneficial to install the sensor node(s) and module(s) with the bulk of the case membrane hidden on the interior side of the garment(s). The sensor node can be placed on the exterior for design purposes. The electrically conductive fabric coupled with the sensor nodes could highlight the garment and provide for some marketing detail. It could also aid in better placement of the sensors. In this format, it could also be somewhat more comfortable for the user.

It may be preferable to place the holster and the sensor module(s) on the exterior of the garment to enable easier access for removal from and attachment to the garment.

(2) Final Sensor Node Installation

Step 1: Gather parts (bonded parts B and C and garment(s) with electrically conductive fabric)

Step 2: Set bonded parts B and C into fixture with the electrically conductive fabric interface remaining visible. There will be a fixture that aligns bonded parts B and C in an orientation that is ergonomic and aligns the sensor node for the next step.

Step 3: Place garment(s) with electrically conductive fabric on top of bonded parts B and C by using its alignment geometry. Guide the pin(s) through the garment(s) with electrically conductive fabric, penetrating the conductive channels.

Step 4: Guide the alignment features of part B through the garment sensor void(s).

Step 5: Bond the bonded parts B and C with part A. Additionally, glue, adhesives, epoxy, RTV, etc. may be applied between the sensor node and sensor modules between the pin(s) and the electrically conductive fabric to promote further sealing for a multiple washing and drying cycles. This process may involve a sonic welder, press, or clamping mechanisms.

(3) Final Sensor Module Installation.

Step 1: Gather parts (parts Q and K and garment(s) with electrically conductive fabric)

Step 2: Set part K into fixture with the electrically conductive fabric interface remaining visible. There will be a fixture that aligns part K in an orientation that is ergonomic and aligns the part for the next step.

Step 3: Place garment(s) with electrically conductive fabric over part K. The alignment features and geometry of part K will help align the garment(s) with bonded electrically conductive fabric onto part K. Move the alignment geometry through the garment sensor void(s).

Step 4: Align part Q using the alignment geometry of part K and allow part Q to rest on top of the assembly.

Step 5: Bond parts K, Q, and the garment(s) with electrically conductive fabric together. Additionally, glue, adhesives, epoxy, RTV, etc. may be applied between the sensor node and sensor modules between the pin(s) and the electrically conductive fabric to promote further sealing for multiple washing and drying cycles. Machines that may be used in this process include a sonic welder, press, or clamping mechanisms.

Various preferred versions of the invention are shown and described above to illustrate different possible features of the invention and the varying ways in which these features may be combined. Apart from combining the different features of the foregoing versions in varying ways, other modifications are also considered to be within the scope of the invention. The invention encompasses at least all different versions that fall literally or equivalently within the scope of the claims.

What is claimed is:

1. A smart garment system including:
a) a garment having a sensor module secured thereto and includes electroluminescent fabric;
b) at least one sensor node having a case membrane, the at least one sensor node connected to the sensor module and containing at least one motion sensor that:
 1) is secured to the garment;
 2) interfaces with the sensor module; and
 3) acquires motion data; and
c) a wireless transmitter configured to send motion data acquired by the at least one motion sensor to a computing device,
wherein the system is configured to provide feedback to a user wearing the garment by luminescing the garment, the feedback being based on the motion data.

2. The system of claim 1 wherein the sensor module includes:
a) a holster permanently secured to the garment; and
b) a removable control unit that secures to the holster.

3. The system of claim 1 wherein the sensor node is permanently fixed to the garment.

4. The system of claim 1 wherein the sensor module is connected to the sensor node via electrically-conductive fabric running along a portion of the garment.

5. The system of claim 4 wherein:
a) the sensor module includes a module case membrane; and
b) the system further includes a module conducting pin extending through a portion of the module case membrane to contact the electrically-conductive fabric so as to allow signals and power to travel from the sensor module via the electrically-conductive fabric.

6. The system of claim 1:
a) further including a first pair of sensor nodes connected to each other in series, and a second pair of sensor nodes connected to each other in series;
b) wherein the first pair of sensor nodes and the second pair of sensor nodes are connected to the sensor module in parallel.

7. The system of claim 1 further including the computing device having a wireless receiver, the computing device being configured to:
a) receive motion data sent by the wireless transmitter; and
b) provide real-time feedback based on the motion data acquired by sensor nodes secured to the garment.

8. The system of claim 7 wherein the real-time feedback includes a 3D avatar representative of a user:
a) wearing the garment; and
b) making movements captured as motion data by the at least one motion sensor.

9. The system of claim 7 wherein the real-time feedback includes voice feedback based on motion data acquired by the at least one or more motion sensors.

10. The system of claim 7 wherein the real-time feedback includes at least one of a graph and a chart with information regarding the movements captured as motion data by the at least one motion sensor.

11. The system of claim 1 further including one or more vibration motors secured to the garment for providing feedback to a user wearing the garment, the vibration motors:
a) being interfaced with the sensor module; and
b) providing real-time coaching feedback to the user based on the motion data acquired by the at least one motion sensor.

12. The system of claim 1 wherein:
a) the garment includes an LED; and
b) the system is configured to provide feedback to a user wearing the garment by turning on the LED, the feedback being based on the motion data.

13. The system of claim 1 wherein at least one motion sensor is connected to the sensor module via electrically conductive fabric.

14. The system of claim 1 wherein:
a) the system further includes at least one of:
1) a 3-axis accelerometer;
2) a 3-axis gyroscope; and
3) a 3-axis magnetometer; and
b) the accelerometer, gyroscope, and/or magnetometer are packaged into one or more sensor nodes positioned on one or more limbs of the garment to acquire data related to orientation.

15. The system of claim 1 further including at least one physiological sensor for acquiring biometric data from a user wearing the garment.

16. The system of claim 1 further including an image capture device having a camera secured to the garment, the image capture device being configured to capture images as a user wearing the garment moves.

17. The system of claim 1 wherein:
a) the garment is a shirt; and
b) the system includes one or more motion sensors secured to the garment on at least one of:
1) both a left wrist segment and a right wrist segment;
2) both a left upper arm segment and a right upper arm segment; and
3) a torso segment.

18. The system of claim 1 wherein:
a) the garment is a pair of pants; and
b) the system includes one or more motion sensors secured to the garment on at least one of:
1) a hip segment;
2) both a left thigh portion and a right thigh segment;
3) both a left shin portion and a right shin portion.

19. The system of claim 1 wherein:
a) the garment is a glove; and
b) the system includes one or more motion sensors secured to the glove on:
1) each of five finger segments;
2) a palm segment; and
3) a back of the hand segment.

20. The system of claim 1 further including one or more motion sensors configured to be secured to a head of a user.

21. The system of claim 1 further including one or more motion sensors configured to be secured to a foot of a user.

22. The system of claim 1 wherein the computing device is not physically secured to the garment.

23. The system of claim 1 further including at least one sensor band having:
a) at least one motion sensor for acquiring motion data; and
b) a transmitter for sending the acquired motion data to at least one of:
1) the sensor module; and
2) the computing device.

24. The system of claim 23 wherein the sensor band is configured to be secured to a user.

25. The system of claim 23 wherein the sensor band is configured to be secured to an object with which a user interacts during an activity.

26. The system of claim 25 wherein the object is a ball used as part of a sport in which the user is participating.

27. A physical training system for fitness or medical applications, the training system including a set of sensor bands configured to be secured to a user, each sensor band having:
a) at least one motion sensor located within a case membrane attached to the sensor band; and
b) a transmitter configured to send motion data to a computing device which is configured to provide, based on the motion data, visual feedback including at least one of:
1) a chart or graph depicting a quantity or quality of motions; and
2) an avatar that simulates movements representing actual or idealized movements of a user.

28. The system of claim 27 further including a garment having a sensor node secured thereto, the sensor node:
a) having at least one motion sensor for acquiring motion data; and
b) being configured to send motion data:
1) to a module secured to the garment via a physical connection; or
2) to another computing device not secured to the garment via a wireless connection.

29. A method of using a physical training system for fitness or medical applications,
a) the training system including a set of sensor bands configured to be secured to a user, each sensor band having:
1) at least one motion sensor located within a case membrane attached to the sensor band; and
2) a transmitter configured to send motion data to another computing device;
b) the method including the step of providing, based on the motion data, visual feedback including at least one of:
1) a chart or graph depicting a quantity or quality of motions; and
2) an avatar that simulates movements representing actual or idealized movements of a user.

* * * * *